(12) United States Patent
Xu

(10) Patent No.: US 12,158,474 B2
(45) Date of Patent: Dec. 3, 2024

(54) METHOD OF CHARACTERIZATION OF VISIBLE AND/OR SUB-VISIBLE PARTICLES IN BIOLOGICS

(71) Applicant: Regeneron Pharmaceuticals, Inc., Tarrytown, NY (US)

(72) Inventor: Xiaobin Xu, White Plains, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/144,463

(22) Filed: May 8, 2023

(65) Prior Publication Data

US 2023/0273219 A1 Aug. 31, 2023

Related U.S. Application Data

(63) Continuation of application No. 17/505,389, filed on Oct. 19, 2021, now Pat. No. 11,693,010, which is a
(Continued)

(51) Int. Cl.
*G01N 33/68* (2006.01)
*G01N 1/28* (2006.01)
(Continued)

(52) U.S. Cl.
CPC ........... *G01N 33/6854* (2013.01); *G01N 1/28* (2013.01); *G01N 21/65* (2013.01); *G01N 30/72* (2013.01);
(Continued)

(58) Field of Classification Search
CPC ...... G01N 33/6854; G01N 1/28; G01N 21/65; G01N 30/72; G01N 33/6848;
(Continued)

(56) References Cited

U.S. PATENT DOCUMENTS 6,214,560 B1 * 4/2001 Yguerabide ......... G01N 33/585
506/3
11,187,707 B2 * 11/2021 Xu ..................... G01N 33/6854
(Continued)

FOREIGN PATENT DOCUMENTS

EP 0233045 A2 8/1987
JP S63502958 A 11/1988
(Continued)

OTHER PUBLICATIONS

John den Engelsman, Strategies for the Assessment of Protein Aggregates in Pharmaceutical Biotech Product Development, Pharm Res, 2011, 28, pp. 920-933, DOI 10.1007/s11095-010-0297-1.
(Continued)

*Primary Examiner* — David A Vanore
(74) *Attorney, Agent, or Firm* — Kramer Levin Naftalis & Frankel LLP

(57) ABSTRACT

A method for characterizing or quantifying one or more proteins in visible and/or sub-visible particles formed in a sample by detecting the at least one visible or sub-visible particle in the sample, isolating and capturing the at least one visible or sub-visible particle to identify a presence of a protein, and using a mass spectrometer to characterize the protein.

26 Claims, 30 Drawing Sheets

Related U.S. Application Data continuation of application No. 16/776,187, filed on Jan. 29, 2020, now Pat. No. 11,187,707.

(60) Provisional application No. 62/798,750, filed on Jan. 30, 2019.

(51) Int. Cl.
| | | |
|---|---|---|
| *G01N 21/65* | (2006.01) | |
| *G01N 30/72* | (2006.01) | |
| *H01J 49/00* | (2006.01) | |
| *H01J 49/02* | (2006.01) | |

(52) U.S. Cl.
CPC ...... *G01N 33/6848* (2013.01); *H01J 49/0031* (2013.01); *H01J 49/02* (2013.01); *G01N 2560/00* (2013.01)

(58) Field of Classification Search
CPC .. G01N 2560/00; H01J 49/0031; H01J 49/02; C07K 1/22
See application file for complete search history.

(56) References Cited

U.S. PATENT DOCUMENTS

| | | | |
|---|---|---|---|
| 11,693,010 B2* | 7/2023 | Xu | G01N 33/6854 250/282 |
| 2002/0161438 A1* | 10/2002 | Scott | A61L 27/50 623/20.14 |
| 2007/0134814 A1* | 6/2007 | Kajander | G01N 33/6893 436/524 |
| 2009/0136937 A1 | 5/2009 | Coleman et al. | |
| 2010/0006495 A1* | 1/2010 | Buschmann | B01D 67/0006 210/500.28 |
| 2010/0216969 A1* | 8/2010 | Snabe | C07K 17/06 530/345 |
| 2016/0060688 A1* | 3/2016 | Coull | C12Q 1/6841 506/9 |
| 2016/0097089 A1* | 4/2016 | Ornatsky | H01J 49/0027 506/9 |
| 2017/0137500 A1 | 5/2017 | Allison et al. | |
| 2018/0340174 A1* | 11/2018 | Lundorf | C12N 15/1065 |
| 2020/0032190 A1* | 1/2020 | Martin | C12N 15/87 |
| 2020/0200760 A1* | 6/2020 | Laury-Kleintop | C07K 17/14 |

FOREIGN PATENT DOCUMENTS

| | | |
|---|---|---|
| JP | 2015-503766 A2 | 2/2015 |
| JP | 2016-519145 A2 | 6/2016 |
| JP | 2016-524711 A2 | 8/2016 |
| JP | 2017-525390 A2 | 9/2017 |
| WO | WO2014186350 A1 | 11/2014 |
| WO | 2017143332 A1 | 8/2017 |
| WO | 2018007456 A1 | 1/2018 |

OTHER PUBLICATIONS

Krista Rule Wigginton, Gold-coated polycarbonate membrane filter for pathogen concentration and SERS-based detection, Analyst, 2010, 135, pp. 1320-1326.

M. Rocchia, Microplastic identification and characterization by Raman imaging spectroscopy, Thermo Fisher Scientific, Nov. 10, 2017, pp. 1-5.

Jared S. Bee, Trace Levels of the CHO Host Cell Protease Cathepsin D Caused Particle Formation in a Monoclonal Antibody Product, Biotechnol. Prog., 2015, vol. 31, No. 5, pp. 1360-1369, DOI 10.1002/btpr.2150.

John Den Engelsman et al: "Strategies for the Assessment of Protein Aggregates in Pharmaceutical Biotech Product Development," Pharmaceutical Research, vol. 28, No. 4, Oct. 23, 2010 (Oct. 23, 2010), pp. 920-933.

Jared S. Bee et al: "Trace levels of the CHO host cell protease cathepsin D caused particle formation in a monoclonal antibody product," Biotechnology Progress, vol. 31, No. 5, Aug. 25, 2015 (Aug. 25, 2015), pp. 1360-1369.

Spela Peternel et al: "New properties of inclusion bodies with implications for biotechnology," Biotechnology and Applied Biochemistry, vol. 49, No. 4, Apr. 1, 2008 (Apr. 1, 2008), p. 239.

International Search Report Application No. PCT/US2020/015699, Filing Date Jan. 29, 2020, Date of Mailing May 12, 2020.

* cited by examiner

Gold coated polycarbonate membrane
5 μm pore size

Protein Particle (~111.7 μm)

Y-axis = Log 2 fold change of protein increased over time

X-axis = Relative abundance of HCPs

Bubble size = protein MW

Coloring = calculated pI

Y-axis = Log 2 fold change of protein increased over time

X-axis = Relative abundance of HCPs

Bubble size = protein MW

Coloring = calculated pI

METHOD OF CHARACTERIZATION OF VISIBLE AND/OR SUB-VISIBLE PARTICLES IN BIOLOGICS

CROSS-REFERENCE TO RELATED APPLICATIONS

This application is a continuation of U.S. patent application Ser. No. 17/505,389, filed on Oct. 19, 2021, which is a continuation of U.S. patent application Ser. No. 16/776,187, filed on Jan. 29, 2020, which is now U.S. Pat. No. 11,187,707, which claims priority to and the benefit of U.S. Provisional Patent Application No. 62/798,750, filed on Jan. 30, 2019, the content of which is incorporated herein by reference in its entirety.

FIELD

The invention generally pertains to a method for characterizing or quantifying one or more proteins in visible and/or sub-visible particles formed in a sample.

BACKGROUND

Protein based biopharmaceutical products have emerged as important drugs for the treatment of cancer, autoimmune disease, infection and cardiometabolic disorders, and they represent one of the fastest growing product segments of the pharmaceutical industry. Robust and stable biopharmaceutical products are a key element in the successful delivery of in the biopharmaceutical industry. A key criterion is the development of formulations essentially free of visible and/or sub-visible particles. Visible and/or sub-visible particles, particularly in such protein based biopharmaceutical products, have been the focus of debate and investigation within the biopharmaceutical industry for several years. Consisting of synthetic or biological materials and originating from various sources, particles can raise the potential for immunogenic effects in patients and may have different effects on the drug product. Thus, it can be important to investigate the origin, composition, and consequences of these particles in order to help reduce or eliminate them from drug products.

When visible and/or sub-visible particles occur in biopharmaceutical products, identification of their composition is a critical step in understanding and mitigating their formation. However, this is a challenging task to determine the workflow and analytical tests since these particles are small, fragile, difficult to isolate, and composed of only a small mass of material. From the foregoing it will be appreciated that a need exists for improved methods for characterizing such visible and/or sub-visible particles that might be formed in a sample.

SUMMARY

A key criterion in developing biopharmaceuticals is to develop formulations that are free of visible and sub-visible particles. When such particles do occur, their identification and quantification can be an important step in the bioprocess.

Exemplary embodiments disclosed herein satisfy the aforementioned demands by providing methods for characterizing, identifying and/or quantifying protein(s) in at least one visible or sub-visible particle in a sample.

This disclosure, at least in part, provides a method for characterization of a protein in at least one visible or sub-visible particle in a sample.

In one exemplary embodiment, the method for characterization of a protein in at least one visible or sub-visible particle in a sample comprises detecting the at least one visible or sub-visible particle in the sample, isolating and capturing the at least one visible or sub-visible particle to identify a presence of a protein, and using a mass spectrometer to characterize the protein.

In one aspect of this embodiment, the method for characterization of a protein in at least one visible or sub-visible particle in a sample can comprise identifying presence of the protein in at least one visible or sub-visible particle using a Raman spectroscopy.

In one aspect of this embodiment, the method for characterization of a protein in at least one visible or sub-visible particle in a sample can comprise at least one visible or sub-visible particle having a size of at least about 5 μm.

In one aspect of this embodiment, the method for characterization of a protein in at least one visible or sub-visible particle in a sample can comprise at least one visible or sub-visible particle comprising an inherent impurity.

In one aspect of this embodiment, the method for characterization of a protein in at least one visible or sub-visible particle in a sample can further comprise capturing the at least one visible or sub-visible particle on a gold-coated polycarbonate membrane.

In one aspect of this embodiment, the method for characterization of a protein in at least one visible or sub-visible particle in a sample can further comprise capturing the at least one visible or sub-visible particle on a gold-coated polycarbonate membrane with a pore size of about 5 μm.

In one aspect of this embodiment, the method for characterization of a protein in at least one visible or sub-visible particle in a sample can further comprise dissolving the sample in urea after identifying the presence of a protein in the at least one visible or sub-visible particle.

In one aspect of this embodiment, the method for characterization of a protein in at least one visible or sub-visible particle in a sample can further comprise dissolving the sample in guanidine hydrochloride after identifying the presence of a protein in the at least one visible or sub-visible particle.

In one aspect of this embodiment, the method for characterization a protein in at least one visible or sub-visible particle in a sample can further comprise dissolving the sample in 8 M urea solution after identifying the presence of a protein in the at least one visible or sub-visible particle.

In one aspect of this embodiment, the method for characterization of a protein in at least one visible or sub-visible particle in a sample can further comprise digesting the sample under denaturing conditions after identifying the presence of a protein in the at least one visible or sub-visible particle.

In one aspect of this embodiment, the method for characterization of a protein in at least one visible or sub-visible particle in a sample can comprise a sample which further comprises a protein of interest.

In one aspect of this embodiment, the method for characterization of a protein in at least one visible or sub-visible particle in a sample can comprise a sample which further comprises an antibody.

In one aspect of this embodiment, the method for characterization of a protein in at least one visible or sub-visible particle in a sample can comprise a sample which further comprises a therapeutic antibody.

In one aspect of this embodiment, the method for characterization of a protein in at least one visible or sub-visible particle in a sample can comprise a liquid chromatography system coupled to a mass spectrometer.

In one aspect of this embodiment, the method for characterization of a protein in at least one visible or sub-visible particle in a sample can comprise a nano liquid chromatography system coupled to a mass spectrometer.

In one aspect of this embodiment, the method for characterization of a protein in at least one visible or sub-visible particle in a sample can comprise using a tandem mass spectrometer to characterize the protein.

In one aspect of this embodiment, the method for characterization of a protein in at least one visible or sub-visible particle in a sample can comprise a protein which is a host-cell protein.

This disclosure, at least in part, provides a method for identification of a protein in at least one visible or sub-visible particle in a sample.

In one exemplary embodiment, the method for identification of a protein in at least one visible or sub-visible particle in a sample comprises detecting the at least one visible or sub-visible particle in the sample, isolating and capturing the at least one visible or sub-visible particle to identify a presence of a protein, and using a mass spectrometer to characterize the protein.

In one aspect of this embodiment, the method for identification of a protein in at least one visible or sub-visible particle in a sample can comprise identifying presence of the protein in at least one visible or sub-visible particle using a Raman spectroscopy.

In one aspect of this embodiment, the method for identification of a protein in at least one visible or sub-visible particle in a sample can comprise at least one visible or sub-visible particle having a size of at least about 5 μm.

In one aspect of this embodiment, the method for identification of a protein in at least one visible or sub-visible particle in a sample can be an inherent impurity.

In one aspect of this embodiment, the method for identification of a protein in at least one visible or sub-visible particle in a sample can further comprise capturing the at least one visible or sub-visible particle on a gold-coated polycarbonate membrane.

In one aspect of this embodiment, the method for identification of a protein in at least one visible or sub-visible particle in a sample can further comprise capturing the at least one visible or sub-visible particle on a gold-coated polycarbonate membrane with a pore size of about 5 μm.

In one aspect of this embodiment, the method for identification of a protein in at least one visible or sub-visible particle in a sample can further comprise dissolving the sample in urea after identifying the presence of a protein in the at least one visible or sub-visible particle.

In one aspect of this embodiment, the method for identification of a protein in at least one visible or sub-visible particle in a sample can further comprise dissolving the sample in 8 M urea solution after identifying the presence of a protein in the at least one visible or sub-visible particle.

In one aspect of this embodiment, the method for identification of a protein in at least one visible or sub-visible particle in a sample can further comprise digesting the sample under denaturing conditions after identifying the presence of a protein in the at least one visible or sub-visible particle.

In one aspect of this embodiment, the method for identification of a protein in at least one visible or sub-visible particle in a sample can comprise a sample which further comprises a protein of interest.

In one aspect of this embodiment, the method for identification of a protein in at least one visible or sub-visible particle in a sample can comprise a sample which further comprises an antibody.

In one aspect of this embodiment, the method for characterization of a protein in at least one visible or sub-visible particle in a sample can comprise a sample which further comprises a therapeutic antibody.

In one aspect of this embodiment, the method for identification of a protein in at least one visible or sub-visible particle in a sample can comprise a liquid chromatography system coupled to a mass spectrometer.

In one aspect of this embodiment, the method for identification of a protein in at least one visible or sub-visible particle in a sample can comprise a nano liquid chromatography system coupled to a mass spectrometer.

In one aspect of this embodiment, the method for identification of a protein in at least one visible or sub-visible particle in a sample can comprise using a tandem mass spectrometer to characterize the protein.

In one aspect of this embodiment, the method for identification of a protein in at least one visible or sub-visible particle in a sample can comprise a protein which is a host-cell protein.

This disclosure, at least in part, provides a method for identification of a host cell-protein in at least one visible or sub-visible particle in a sample.

In one exemplary embodiment, the a method for identification of a host cell-protein in at least one visible or sub-visible particle in a sample comprises detecting at least one visible or sub-visible particle in the sample, isolating and capturing the at least one visible or sub-visible particle to identify a presence of a protein, and using a mass spectrometer to characterize the protein to determine if the protein is the host cell-protein.

In one aspect of this embodiment, the identification of a host cell-protein in at least one visible or sub-visible particle in a sample can comprise identifying the host-cell protein in at least one visible or sub-visible particle using a Raman spectroscopy.

In one aspect of this embodiment, the identification of a host cell-protein in at least one visible or sub-visible particle in a sample can comprise at least one visible or sub-visible particle having a size of at least about 5 μm.

In one aspect of this embodiment, the method for characterization of a protein in at least one visible or sub-visible particle in a sample can comprise a host-cell protein which can be an inherent impurity.

In one aspect of this embodiment, the method of identification of a host cell-protein in at least one visible or sub-visible particle in a sample can further comprise capturing the at least one visible or sub-visible particle on a gold-coated polycarbonate membrane.

In one aspect of this embodiment, the method for identification of a host cell-protein in at least one visible or sub-visible particle in a sample can further comprise capturing the at least one visible or sub-visible particle on a gold-coated polycarbonate membrane with a pore size of about 5 μm.

In one aspect of this embodiment, the method for identification of a host cell-protein in at least one visible or sub-visible particle in a sample can further comprise dissolving the sample in urea after identifying the presence of a host-cell protein in the at least one visible or sub-visible particle.

In one aspect of this embodiment, the method for identification of a host cell-protein in at least one visible or sub-visible particle in a sample can further comprise dissolving the sample in 8 M urea solution after identifying the presence of a host-cell protein in the at least one visible or sub-visible particle.

In one aspect of this embodiment, the method for identification of a host cell-protein in at least one visible or sub-visible particle in a sample can further comprise digesting the sample under denaturing conditions after identifying the presence of a host-cell protein in the at least one visible or sub-visible particle.

In one aspect of this embodiment, the method for identification of a host cell-protein in at least one visible or sub-visible particle in a sample can comprise a sample which further comprises a protein of interest.

In one aspect of this embodiment, the method for characterization of a protein in at least one visible or sub-visible particle in a sample can comprise a sample which further comprises an antibody.

In one aspect of this embodiment, the method for identification of a host cell-protein in at least one visible or sub-visible particle in a sample can comprise a sample which further comprises a therapeutic antibody.

In one aspect of this embodiment, the method for identification of a host cell-protein in at least one visible or sub-visible particle in a sample can comprise a liquid chromatography system coupled to a mass spectrometer.

In one aspect of this embodiment, the method for identification of a host cell-protein in at least one visible or sub-visible particle in a sample can comprise a nano liquid chromatography system coupled to a mass spectrometer.

In one aspect of this embodiment, the method for identification of a host cell-protein in at least one visible or sub-visible particle in a sample can comprise using a tandem mass spectrometer to characterize the protein.

In one aspect of this embodiment, the method for identification of a host cell-protein in at least one visible or sub-visible particle in a sample can comprise a protein which is a host-cell protein.

DETAILED DESCRIPTION

Presence of visible and sub-visible particles is a major issue during formulation of drug products comprising proteins. These particles can be either proteinaceous or non-proteinaceous and need to be analyzed to monitor the stability of the formulation. Increasing concerns about the immunogenic potential of such particles in drug products require a robust method and/or workflow to characterize its content.

Figure 1:
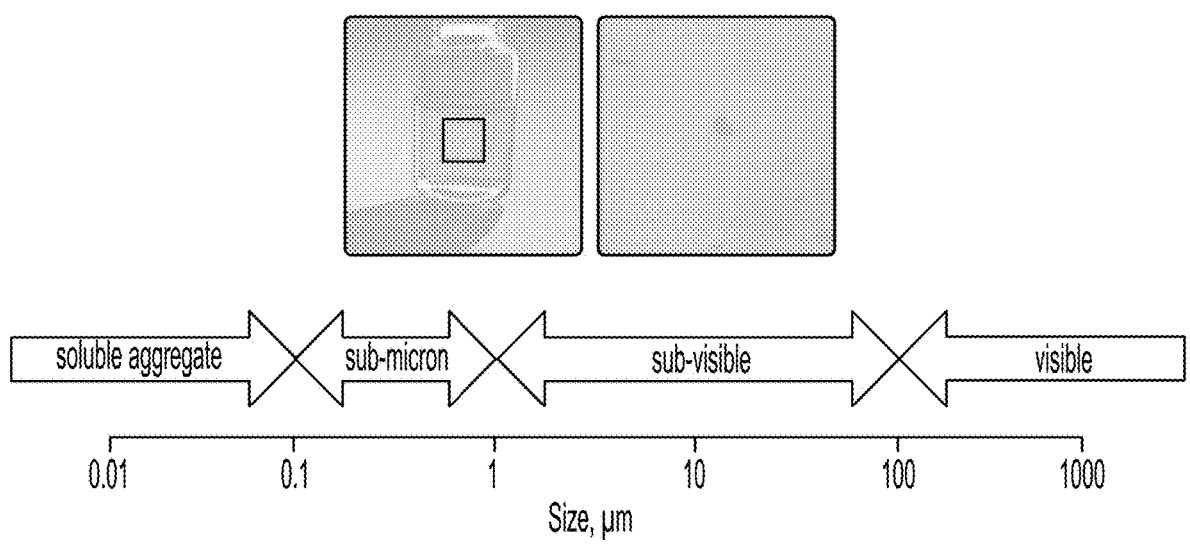
FIG. 1 shows the range of particle sizes of particles found in drug products (in microns).

A major challenge during formulation development of drug products comprising proteins, is overcoming their limited stability. Aggregation is one of the most serious degradation mechanisms. Aggregates can vary in many aspects such as size, reversibility, and structure. For instance, their size can range from dimers in the nanometer range to large aggregates of hundreds of microns, which are visible to the human eye (See FIG. 1). The aggregates can comprise proteinaceous as well as non-proteinaceous particles, for example, originating from packaging material or excipients influencing product quality and therefore need to be analyzed.

As disclosed in U.S. Pharmacopeia, the chapters designated for "Visible Particulates in injections <790>" and "subvisible Particulate Matter in Therapeutic Protein Injections <1787>" aid in providing a general guidance on particulate matter content of drug products. The types of particulate matter that can be present in drug products are outlined in FIG. 2.

Figure 2:
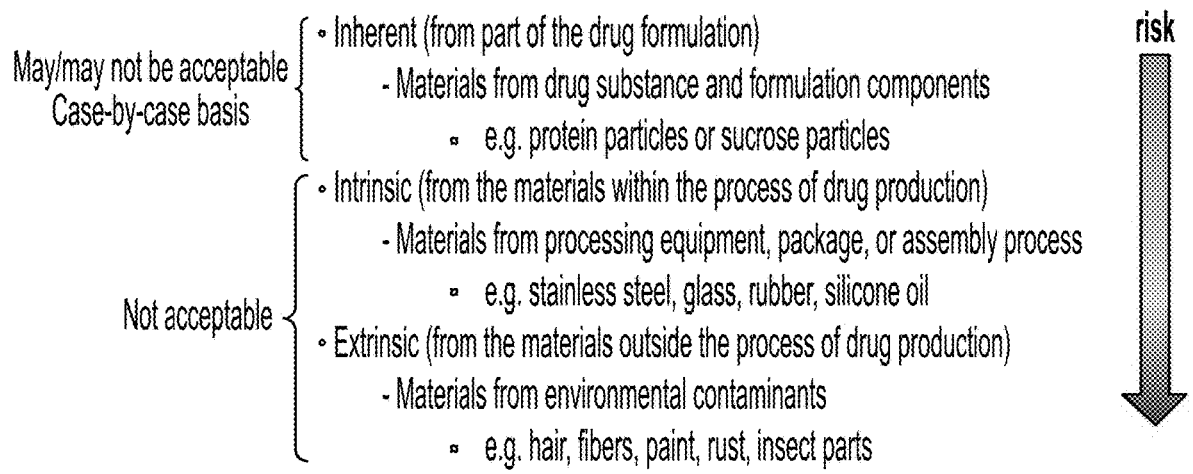
FIG. 2 shows the types of particulate matter in drug products.
Figure 3:
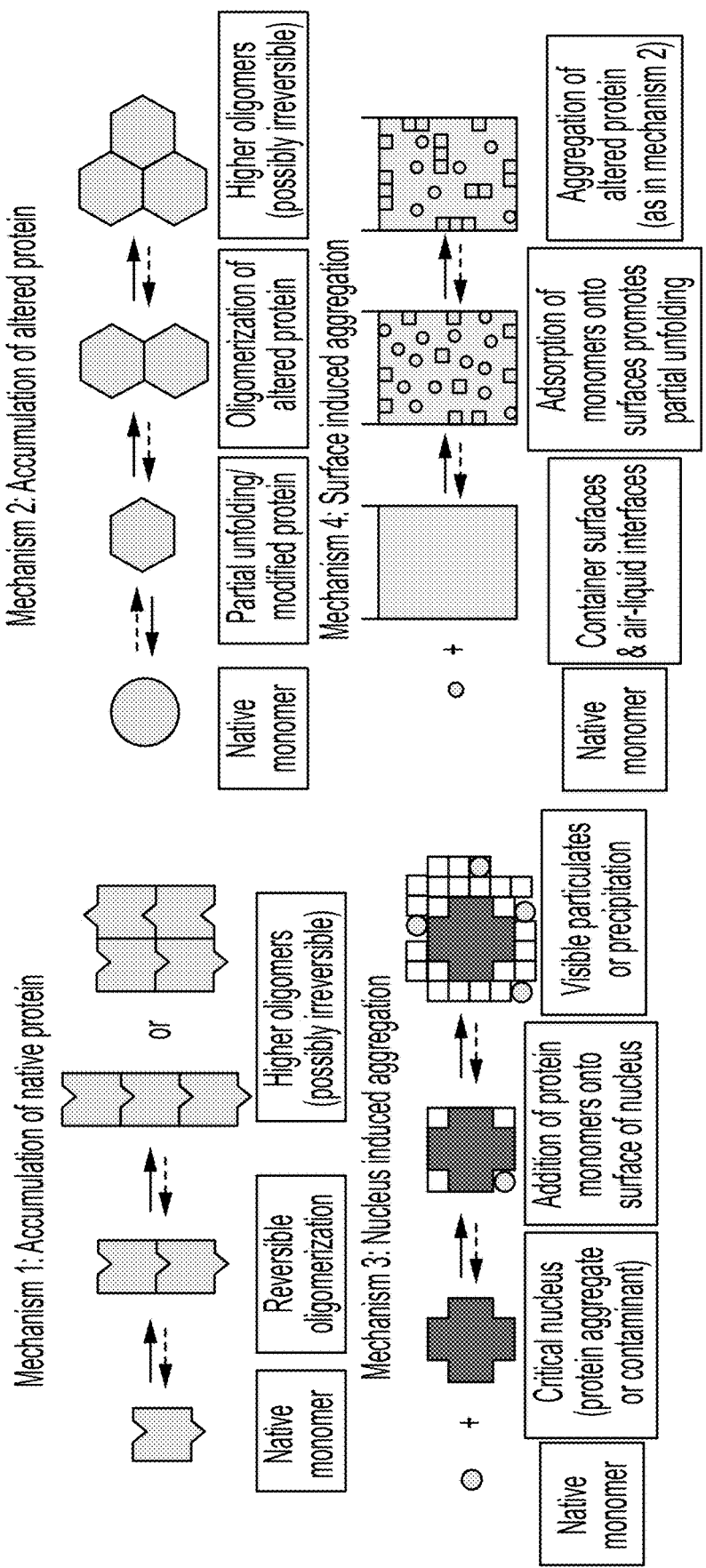
FIG. 3 shows a schematic scheme of common mechanism of protein aggregates.

Inherent particulate matter in drug products as shown in FIG. 2 can comprise aggregated protein. The aggregation can be formed due to different types of different mechanisms and pathways (See FIG. 3). These mechanisms are not mutually exclusive and can occur in parallel within the same product (John Philo & Tsutomu Arakawa, *Mechanisms of Protein Aggregation*, 10 CURRENT PHARMACEUTICAL BIOTECHNOLOGY 348-351 (2009)). The predominant mechanisms depends not only on the protein itself, but also on a variety of other factors, such as the formulation, the presence of impurities or contaminants, and the exposure to chemical or physical stress mentioned above. It is currently not fully understood how different aggregation mechanisms and the thereby resulting structural differences of aggregates influence their potential immunogenicity.

Figure 4:
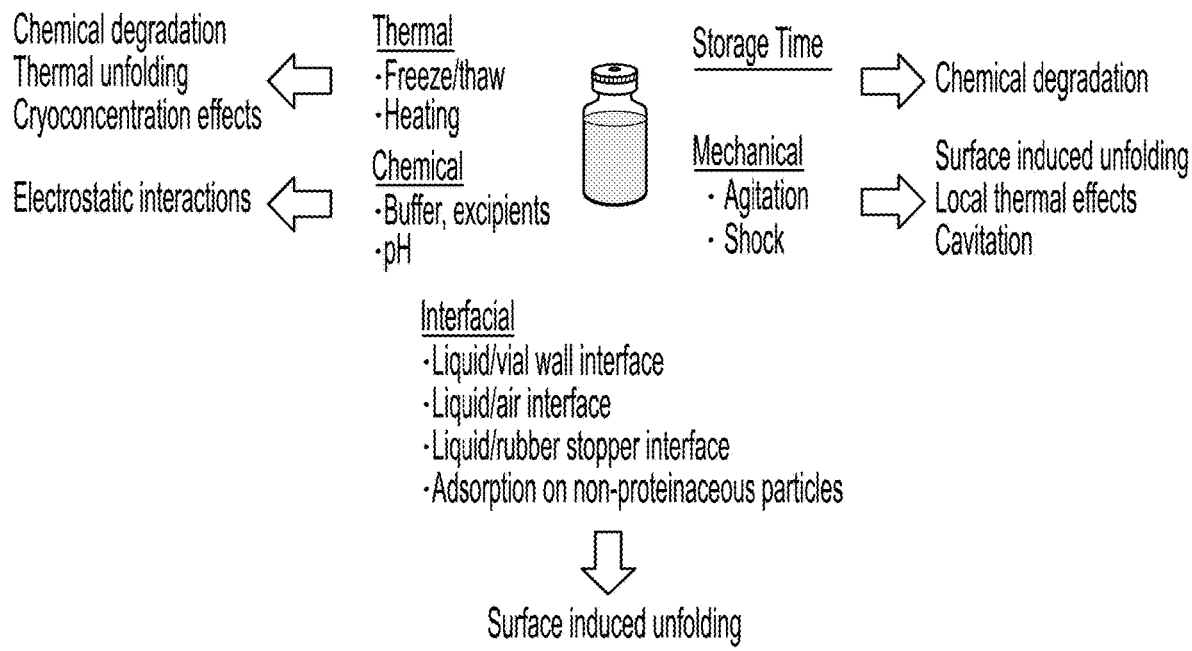
FIG. 4 lists the potential causes of particle formation in drug products.

Some of the potential causes of particle formation in drug products, listed in FIG. 4, are namely due to thermal stress, degradation during storage time, chemical degradation of the excipients in the drug product, mechanical stress, and interfacial stress. Potential consequences of such particles in drug products can render the product unsafe (cause capillary blood vessel occlusion, immunogenicity, or cytotoxicity), alter the efficacy (cause hypo- or hyper-potency or change the biodistribution and clearance of the drug in the body), alter the pharmacokinetics of the drug, render the product inconsistent, or render the bioprocess inconsistent.

Figure 5:
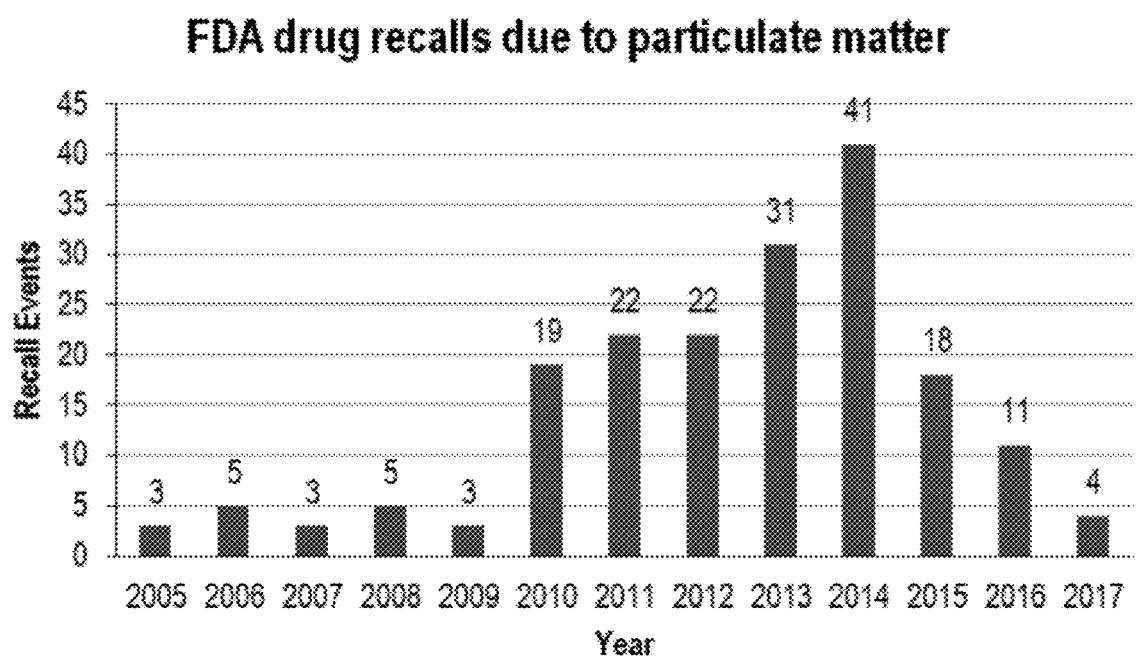
FIG. 5 shows the graph of FDA drug recalls due to particulate matter over the years 2005-2017.
Figure 6:
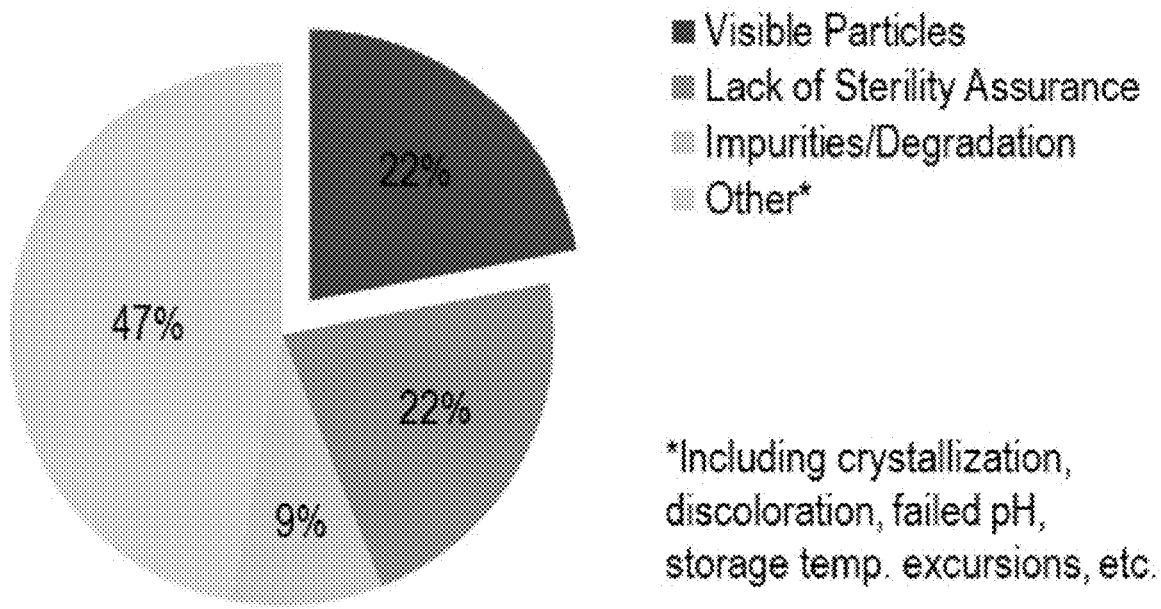
FIG. 6 shows the chart showing the reasons for FDA sterile injectable drug recalls from the years 2008 to 2012.

FDA recalls of injectable drugs suggest that particulate matter is one of the main reasons for drug recalls (See FIG. 5). From the years 2008-2012, the presence of visible particles accounted for 22% of recalls among sterile injectable drugs (See FIG. 6).

Regulatory bodies require drug product analysis for particulate matter to include visible and sub-visible particle analysis as a part of product characterization and control and a risk assessment should be included to assess their potential impact on safety and efficacy. The analyses also involve multiple stress conditions for assessment of propensity to form particulate matter and stability evaluation. Following such analyses, strategies are required to be implemented to minimize the formation of particulate matter. For visible particles, the U. S. Pharmacopeia (U.S.P.) guidance on testing particulate matter lists (i) requirement of 100% visual inspection at filling process (USP <1> Injections), (ii) guidance for 100% visual inspection (USP <790> Visible Particulates in Injections), and (iii) description of inspector training, sampling methods, and inspection; emphasizes prevention/inspection lifecycle (USP <1790> Visual Inspection of Injections). The U. S. Pharmacopeia (U.S.P.) also lists guidance on testing particulate matter for sub-visible particles, such as, (i) the limits for sub-visible particles ($\geq 10$ µm particles $\leq 25$ per ml; $\geq 25$ µm particles $\leq 3$ per mil) and recommendation of the two methods, light obscuration and microscopy, for particle counting (USP <788> Particulate Matter in Injections), (ii) specific requirement for Biologicals and discontinuation of use of microscopy for counting proteinaceous particles (USP <787> Subvisible Particulate Matter in Therapeutic Protein Injections), and (iii) methods to distinguish types of particles; emphasis on characterization of proteinaceous particles (USP <1787> Measurement of Subvisible Particulate Matter in Therapeutic Protein Injections). Lastly, for particulate Matter in Ophthalmic Solutions, the U. S. Pharmacopeia (U.S.P.) guidance on testing particulate matter provides guidance in chapters USP <789> Particulate Matter in Ophthalmic Solutions and USP <1788> Methods for the Determination of Particulate Matter in Injections and Ophthalmic Solutions.

One of the major challenges during protein formulation development and evaluation is characterization and quantification of potential degradation products, particularly aggregates and particles (Linda Narhi, Jeremy Schmit & Deepak Sharma, Classification of protein aggregates, 101 JOURNAL OF PHARMACEUTICAL SCIENCES 493-498 (2012)).

While instrument manufacturers have worked on providing new analytical techniques to overcome an analytical gap in the sub-visible size range, there is a large demand of establishing a workflow to aid their critical scientific evaluation.

Considering the limitations of existing methods, an effective and efficient method for identification and characterization of visible or sub-visible particles in a drug product was developed.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

The term "a" should be understood to mean "at least one"; and the terms "about" and "approximately" should be understood to permit standard variation as would be understood by those of ordinary skill in the art; and where ranges are provided, endpoints are included.

In some exemplary embodiments, the disclosure provides a method for characterization of a protein in at least one visible or sub-visible particle in a sample.

As used herein, the term "protein" includes any amino acid polymer having covalently linked amide bonds. Proteins comprise one or more amino acid polymer chains, generally known in the art as "polypeptides". "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides' refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may contain one or multiple polypeptides to form a single functioning biomolecule. A protein can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. In another exemplary aspect, a protein can include antibody fragments, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a review discussing biotherapeutic proteins and their production, see Ghaderi et al., "Production platforms for biotherapeutic glycoproteins. Occurrence, impact, and challenges of non-human sialylation," (BIOTECHNOL. GENET. ENG. REV. 147-175 (2012)). In some exemplary embodiments, proteins comprise modifications, adducts, and other covalently linked moieties. Those modifications, adducts and moieties include for example avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as, nucleoproteins, glycoproteins, mucoproteins, chromoproteins, phosphoproteins, metalloproteins, and lipoproteins; and derived proteins, such as, primary derived proteins and secondary derived proteins.

In some exemplary embodiments, the protein can be an antibody, a bispecific antibody, a multispecific antibody, antibody fragment, monoclonal antibody, host-cell protein or combinations thereof.

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_{H2}$ and $C_H3$. Each light chain comprises a light chain variable region (abbreviated herein as LCVR or $V_L$) and a light chain constant region. The light chain constant region comprises one domain (C.sub.L1). The $V_H$ and $V_L$ regions can be further subdivided into regions of hypervariability, termed complementarity determining regions (CDRs), interspered with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different exemplary embodiments, the FRs of the anti-big-ET-1 antibody (or antigen-binding portion thereof) may be identical to the human germline sequences, or may be naturally or artificially modified. An amino acid consensus sequence may be defined based on a side-by-side analysis of two or more CDRs. The term "antibody," as used herein, also includes antigen-binding fragments of full antibody molecules.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a Fc fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. An antibody fragment may be produced by various means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

As used herein, the term "host-cell protein" includes protein expressed by the host cell and can be unrelated to the desired protein of interest. Host-cell protein can be a process-related impurity which can be derived from the manufacturing process and can include the three major categories: cell substrate-derived, cell culture-derived and downstream derived. Cell substrate-derived impurities include, but are not limited to, proteins derived from the host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables.

In some exemplary embodiments, the at least one visible or sub-visible particle can comprise a process related impurity.

In some exemplary embodiments, the at least one visible or sub-visible particle can comprise a product related impurity.

As used herein, "product-related impurities" (e.g., precursors, certain degradation products) can be molecular variants arising during manufacture and/or storage that do not have properties comparable to those of the desired product with respect to activity, efficacy, and safety. Such variants may need considerable effort in isolation and characterization in order to identify the type of modification(s). Product-related impurities can include truncated forms, modified forms, and aggregates. Truncated forms are formed by hydrolytic enzymes or chemicals which catalyze the cleavage of peptide bonds. Modified forms include, but are not limited to, deamidated, isomerized, mismatched S-S linked, oxidized, or altered conjugated forms (e.g., glycosylation, phosphorylation). Modified forms can also include any post-translational modification form. Aggregates include dimers and higher multiples of the desired product. (Q6B Specifications: Test Procedures and Acceptance Criteria for Biotechnological/Biological Products, ICH August 1999, U.S. Dept. of Health and Humans Services).

In some exemplary embodiments, the visible or sub-visible particle can comprise protein aggregate. As used herein, the term "protein aggregate" refers to assemblies of protein monomers which can vary in size, reversibility, and structure. Some of the mechanisms of protein aggregate formation are outlined in FIG. 4.

As used herein, the term "formulation" refers to an active pharmaceutical agent that is formulated together with one or more pharmaceutically acceptable vehicles.

As used herein, the term "an active pharmaceutical agent" can include a biologically active component of a drug product. An active pharmaceutical agent can refer to any substance or combination of substances used in a drug product, intended to furnish pharmacological activity or to otherwise have direct effect in the diagnosis, cure, mitigation, treatment or prevention of disease, or to have direct effect in restoring, correcting or modifying physiological functions in animals. Non-limiting methods to prepare an active pharmaceutical agent can include using fermentation process, recombinant DNA, isolation and recovery from natural resources, chemical synthesis, or combinations thereof.

In some exemplary embodiments, the formulation can be a protein formulation.

As used herein, the term "protein formulation" refers to a therapeutic protein that is formulated together with one or more pharmaceutically acceptable vehicles. In some embodiments, the therapeutic protein is present in a unit dose amount appropriate for administration in a therapeutic regimen.

In some other embodiments, the formulation can further comprise excipients including, but not limited to buffering agents, bulking agents, tonicity modifiers, surfactants, solubilizing agents, and preservatives. Other additional excipients can also be selected based on function and compatibility with the formulations may be found, for example in LOYD V. ALLEN, REMINGTON: THE SCIENCE AND PRACTICE OF PHARMACY (19 ed. 1995), JOHN E HOOVER, REMINGTON'S PHARMACEUTICAL SCIENCES (1975), and LYOD ALLEN, ANSEL'S PHARMACEUTICAL DOSAGE FORMS AND DRUG DELIVERY SYSTEMS (10 ed.) herein incorporated by reference in their entirety.

In some exemplary embodiments, the formulation can be stable.

The stability of a formulation can comprise evaluating the chemical stability, physical stability or functional stability of the active pharmaceutical agent. The formulations of the present invention typically exhibit high levels of stability of the active pharmaceutical agent.

In terms of protein formulations, the term "stable," as used herein, refers to the proteins within the formulations that can retain an acceptable degree of chemical structure or biological function after storage under exemplary conditions described herein. A formulation may be stable even though the protein contained therein does not maintain 100% of its chemical structure or biological function after storage for a defined amount of time. Under certain circumstances, maintenance of about 90%, about 95%, about 96%, about 97%, about 98% or about 99% of a protein's structure or function after storage for a defined amount of time may be regarded as "stable".

In some exemplary embodiments, the fatty acid particles can be at least 5 µm in size. Further, these fatty acid particles can be classified according to their size as visible (>100 µm), sub-visible (<100 µm, which can be sub-divided into micron (1-100 µm) and submicron (100 nm-1000 nm)) and nanometer particles (<100 nm) (Linda Narhi, Jeremy Schmit & Deepak Sharma, Classification of protein aggregates, 101 JOURNAL OF PHARMACEUTICAL SCIENCES 493-498 (2012)).

In some exemplary embodiments, the particles can be detected as protein by Raman Spectroscopy. As used herein, the term "Raman spectroscopy" refers to a spectroscopic method based on Raman scattering method. Raman Spectroscopy can provide a Raman spectrum, which can identify the presence and position of bands in the fingerprint region (2000 to 400 $cm^{-1}$) which enables the chemical identification of the analyzed material by comparison with a database of Raman spectra (C. V. Raman and K. S. Krishnan, A new type of secondary radiation. 121 NATURE 501-502 (1928); Zai-Qing Wen, Raman spectroscopy of protein pharmaceuticals, 96 JOURNAL OF PHARMACEUTICAL SCIENCES 2861-287 (2007)).

As used herein, the term "chromatography" refers to a process in which a chemical mixture carried by a liquid or gas can be separated into components as a result of differential distribution of the chemical entities as they flow around or over a stationary liquid or solid phase. Non-limiting examples of chromatography include traditional reversed-phased (RP), ion exchange (IEX) and normal phase chromatography (NP). Unlike RP, NP and IEX chromatography, in which hydrophobic interaction, hydrophilic interaction and ionic interaction respectively are the dominant interaction modes, mixed-mode chromatography can employ a combination of two or more of these interaction modes.

As used herein, the term "mass spectrometer" includes a device capable of identifying specific molecular species and measuring their accurate masses. The term is meant to include any molecular detector into which a polypeptide or peptide may be eluted for detection and/or characterization. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends heavily on the application.

As used herein, the term "mass analyzer" includes a device that can separate species, that is, atoms, molecules, or clusters, according to their mass. Non-liming examples of mass analyzers that could be employed for fast protein sequencing are time-of-flight (TOF), magnetic/electric sector, quadrupole mass filter (Q), quadrupole ion trap (QIT), orbitrap, Fourier transform ion cyclotron resonance (FTICR), and also the technique of accelerator mass spectrometry (AMS).

As used herein, the term "tandem mass spectrometry" includes a technique where structural information on sample molecules is obtained by using multiple stages of mass selection and mass separation. A prerequisite is that the sample molecules can be transferred into gas phase and ionized intact and that they can be induced to fall apart in some predictable and controllable fashion after the first mass selection step. Multistage MS/MS, or $MS^n$, can be performed by first selecting and isolating a precursor ion ($MS^2$), fragmenting it, isolating a primary fragment ion ($MS^3$), fragmenting it, isolating a secondary fragment ($MS^4$), and so on as long as one can obtain meaningful information or the fragment ion signal is detectable. Tandem MS has been successfully performed with a wide variety of analyzer combinations. What analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time, mass spectrometer ions produced in the ion source can be trapped, isolated, fragmented, and m/z separated in the same physical device.

The peptides identified by the mass spectrometer can be used as surrogate representatives of the intact protein and their post translational modifications. They can be used for protein characterization by correlating experimental and theoretical MS/MS data, the latter generated from possible peptides in a protein sequence database. The characterization includes, but is not limited to, sequencing amino acids of the protein fragments, determining protein sequencing, determining protein de novo sequencing, locating post-translational modifications, or identifying post translational modifications, or comparability analysis, or combinations thereof.

As used herein, the term "database" refers to bioinformatic tools which provide the possibility of searching the uninterested MS-MS spectra against all possible sequences in the database(s). Non-limiting examples of such tools are Mascot (http://www.matrixscience.com), Spectrum Mill (http://www.chem.agilent.com), PLGS (http://www.waters.com), PEAKS (http://www.bioinformaticssolutions.com), Proteinpilot (http://download.appliedbiosystems.com//proteinpilot), Phenyx (http://www.phenyx-ms.com), Sorcerer (http://www.sagenresearch.com), OMSSA (http://www.pubchem.ncbi.nlm.nih.gov/omssa/), X!Tandem (http://www.thegpm.org/TANDEM/), Protein Prospector (http://www. http://prospector.ucsf.edu/prospector/mshome.htm), Byonic (https://www.proteinmetrics.com/products/byonic) or Sequest (http://fields.scripps.edu/sequest).

EXEMPLARY EMBODIMENTS

Embodiments disclosed herein provide compositions, methods, and systems for the rapid characterization of proteins in a sample.

In some exemplary embodiments, this disclosure provides a method for characterization of a protein in at least one visible or sub-visible particle in a sample, comprising detecting the at least one visible or sub-visible particle in the sample, isolating and capturing the at least one visible or sub-visible particle to identify a presence of a protein, and using a mass spectrometer to characterize the protein.

In some exemplary embodiments, this disclosure provides a method for identification of a protein in at least one visible or sub-visible particle in a sample, comprising detecting the at least one visible or sub-visible particle in the sample, isolating and capturing the at least one visible or sub-visible particle to identify a presence of a protein, and using a mass spectrometer to characterize the protein.

In some exemplary embodiments, this disclosure provides a method for identification of a host cell-protein in at least one visible or sub-visible particle in a sample, comprising detecting at least one visible or sub-visible particle in the sample, isolating and capturing the at least one visible or sub-visible particle to identify a presence of a protein, and using a mass spectrometer to characterize the protein to determine if the protein is the host cell-protein.

In some exemplary embodiments, Raman spectroscopy can be used to identify the presence of the protein in at least one visible or sub-visible particle.

In some exemplary embodiments, the at least one visible or sub-visible particle can have a size of at least about 2 µm. In one aspect, the at least one visible or sub-visible particle can have a size of at least about 2 µm, at least about 3 µm, at least about 4 µm, at least about 5 µm, at least about 6 µm, at least about 7 µm, at least about 8 µm, at least about 9 µm, at least about 10 µm, at least about 11 µm, at least about 12 µm, at least about 13 µm, at least about 14 µm, at least about 15 µm, at least about 20 µm, at least about 25 µm, at least about 30 µm, at least about 35 µm, at least about 40 µm, at least about 45 µm, at least about 50 µm, at least about 55 µm, at least about 60 µm, at least about 65 µm, at least about 70 µm, at least about 7 µm, at least about 80 µm, at least about 85 µm, at least about 90 µm, at least about 95 µm, or at least about 100 µm.

In some exemplary embodiments, the protein can be an inherent impurity.

In some exemplary embodiments, the at least one visible or sub-visible particle can be captured on a gold-coated polycarbonate membrane. In some exemplary embodiments, the gold-coated polycarbonate membrane can have a pore size of about 5 μm.

In some exemplary embodiments, the at least one visible or sub-visible particle can be captured on a filter paper. In some exemplary embodiments, the filter paper can have a pore size of about 5 μm.

In some exemplary embodiments, the method can further comprise excising a portion of a gold-coated polycarbonate membrane or a filter paper used to capture the at least one visible or sub-visible particle.

In some exemplary embodiments, the method can further comprise dissolving the sample in urea after identifying the presence of a protein or a host-cell protein in the at least one visible or sub-visible particle. In one aspect, the sample can be dissolved in 8 M urea solution.

In some exemplary embodiments, the method can further comprise denaturing the sample under denaturing conditions after identifying the presence of a protein or a host-cell protein in the at least one visible or sub-visible particle. In one aspect, the sample can be denatured using dithiothreitol at a suitable temperature.

In some exemplary embodiments, the method can further comprise digesting the sample under denaturing conditions after identifying the presence of a protein or a host-cell protein in the at least one visible or sub-visible particle. In one aspect, the sample can be digested using a hydrolyzing agent. Non-limiting examples of hydrolyzing agents that can carry out enzymatic digestion include trypsin, endoproteinase Arg-C, endoproteinase Asp-N, endoproteinase Glu-C, outer membrane protease T (OmpT), immunoglobulin-degrading enzyme of *Streptococcus pyogenes* (IdeS), chymotrypsin, pepsin, thermolysin, papain, pronase, and protease from *Aspergillus Saitoi*. Non-limiting examples of hydrolyzing agents that can carry out non-enzymatic digestion include the use of high temperature, microwave, ultrasound, high pressure, infrared, solvents (non-limiting examples are ethanol and acetonitrile), immobilized enzyme digestion (IMER), magnetic particle immobilized enzymes, and on-chip immobilized enzymes. For a recent review discussing the available techniques for protein digestion see Switazar et al., "Protein Digestion: An Overview of the Available Techniques and Recent Developments" (J. Proteome Research 2013, 12, 1067-1077). One or a combination of hydrolyzing agents can cleave peptide bonds in a protein or polypeptide, in a sequence-specific manner, generating a predictable collection of shorter peptides.

In some exemplary embodiments, the sample can further comprise a protein of interest. In one aspect, the protein of interest can be a therapeutic antibody, an antibody, a monoclonal antibody, a polyclonal antibody, a bispecific antibody, an antibody fragment, a fusion protein, or combination thereof.

In one exemplary embodiment, the protein or host-cell protein can be a post-translationally modification of protein of interest. The various post-translational modifications include, but are not limited to, cleavage, N-terminal extensions, protein degradation, acylation of the N-terminus, biotinylation (acylation of lysine residues with a biotin), amidation of the C-terminal, glycosylation, iodination, covalent attachment of prosthetic groups, acetylation (the addition of an acetyl group, usually at the N-terminus of the protein), alkylation (the addition of an alkyl group (e.g. methyl, ethyl, propyl) usually at lysine or arginine residues), methylation, adenylation, ADP-ribosylation, covalent cross links within, or between, polypeptide chains, sulfonation, prenylation, Vitamin C dependent modifications (proline and lysine hydroxylations and carboxy terminal amidation), Vitamin K dependent modification wherein Vitamin K is a cofactor in the carboxylation of glutamic acid residues resulting in the formation of a γ-carboxyglutamate (a glu residue), glutamylation (covalent linkage of glutamic acid residues), glycylation (covalent linkage glycine residues), glycosylation (addition of a glycosyl group to either asparagine, hydroxylysine, serine, or threonine, resulting in a glycoprotein), isoprenylation (addition of an isoprenoid group such as farnesol and geranylgeraniol), lipoylation (attachment of a lipoate functionality), phosphopantetheinylation (addition of a 4'-phosphopantetheinyl moiety from coenzyme A, as in fatty acid, polyketide, non-ribosomal peptide and leucine biosynthesis), phosphorylation (addition of a phosphate group, usually to serine, tyrosine, threonine or histidine), and sulfation (addition of a sulfate group, usually to a tyrosine residue).

The post-translational modifications that change the chemical nature of amino acids include, but are not limited to, citrullination (the conversion of arginine to citrulline by deimination), and deamidation (the conversion of glutamine to glutamic acid or asparagine to aspartic acid).

The post-translational modifications that involve structural changes include, but are not limited to, formation of disulfide bridges (covalent linkage of two cysteine amino acids) and proteolytic cleavage (cleavage of a protein at a peptide bond). Certain post-translational modifications involve the addition of other proteins or peptides, such as ISGylation (covalent linkage to the ISG15 protein (Interferon-Stimulated Gene)), SUMOylation (covalent linkage to the SUMO protein (Small Ubiquitin-related MOdifier)) and ubiquitination (covalent linkage to the protein ubiquitin). See http://www.uniprot.org/docs/ptmlist for a more detailed controlled vocabulary of PTMs curated by UniProt.

In another exemplary embodiment, the sample can be obtained from any step of the bioprocess, such as, culture cell culture fluid (CCF), harvested cell culture fluid (CCF), process performance qualification (PPQ), any step in the downstream processing, drug solution (DS), or a drug product (DP) comprising the final formulated product. In some other specific exemplary embodiments, the sample can be selected from any step of the downstream process of clarification, chromatographic purification, viral inactivation, or filtration. In one aspect, the drug product can be selected from manufactured drug product in the clinic, shipping, storage, or handling.

In some exemplary embodiments, the mass spectrometer can be coupled to a liquid chromatography. In one aspect, the mass spectrometer can be coupled to a nano liquid chromatography. In some exemplary embodiments, the mobile phase used to elute the protein in liquid chromatography can be a mobile phase that can be compatible with a mass spectrometer. In one aspect, the mobile phase can be ammonium acetate, ammonium bicarbonate, or ammonium formate, or combinations thereof.

In another exemplary embodiment, the mass spectrometer can comprise a nanospray.

In some exemplary embodiments, the mass spectrometer can be a tandem mass spectrometer to characterize the protein.

In some exemplary embodiments, the protein or host-cell protein can be a therapeutic antibody, an antibody, a monoclonal antibody, a polyclonal antibody, a bispecific antibody, an antibody fragment, a fusion protein, or combinations thereof. In one aspect, the antibody fragment can include Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, triabodies, tetrabodies, linear antibodies, single-chain antibody molecules, and multi specific antibodies formed from antibody fragments.

In some exemplary embodiments, the protein or host-cell protein can be a digestion product of the antibody. The digestion product can be formed by a hydrolyzing agent. The digestion product can be a product-related impurity.

In some exemplary embodiments, the protein or host-cell protein can have a pI in the range of about 4.5 to about 9.0. In one exemplary specific embodiment, the protein can have a pI of about 4.5, about 5.0, about 5.5, about 5.6, about 5.7, about 5.8, about 5.9, about 6.0, about 6.1 about 6.2, about 6.3, about 6.4, about 6.5, about 6.6, about 6.7, about 6.8, about 6.9, about 7.0, about 7.1 about 7.2, about 7.3, about 7.4, about 7.5, about 7.6, about 7.7, about 7.8, about 7.9, about 8.0, about 8.1 about 8.2, about 8.3, about 8.4, about 8.5, about 8.6, about 8.7, about 8.8, about 8.9, or about 9.0.

In one exemplary embodiment, the number of visible or sub-visible particles in the sample can be at least two.

In one exemplary embodiment, the types of protein or host-cell protein in the visible or sub-visible particle can be at least two.

It is understood that the methods are not limited to any of the aforesaid protein, impurity, column and that the methods for identifying or quantifying may be conducted by any suitable means.

Figure 7:
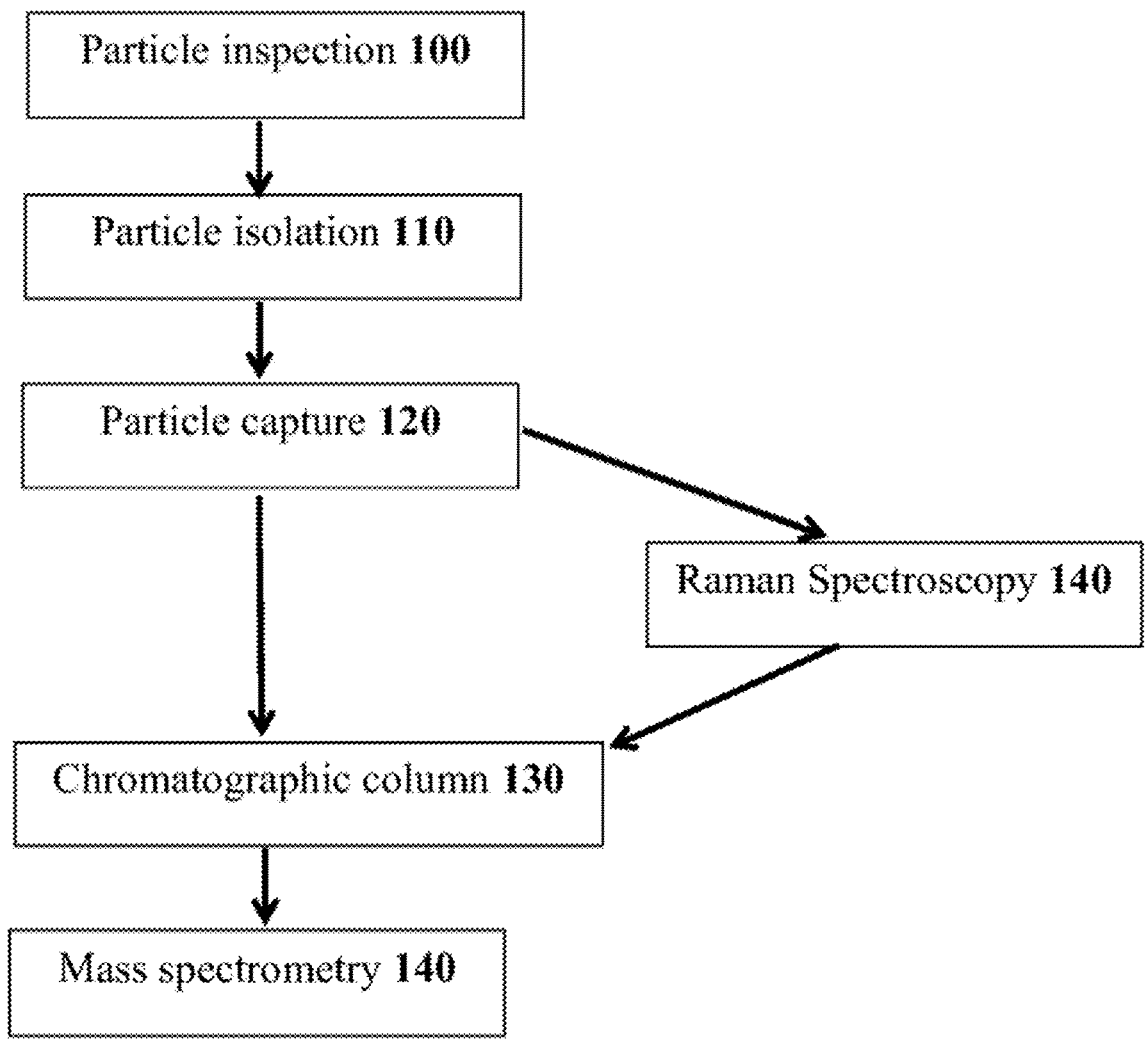
FIG. 7 shows two workflows for characterization of a protein or host-cell protein according to an exemplary embodiment.

In some exemplary embodiments, the disclosure provides a workflow comprising a particle inspection 100, particle isolation 110, particle capture 120, and a mass spectrometer 140 coupled to the chromatographic column 130 (See FIG. 7).

In some exemplary embodiments, the workflow can further comprise Raman spectroscopy 150 capable of identifying presence of a protein.

In some exemplary embodiments, the particle inspection 100 can be performed by visual inspection, light obscuration, or micro flow imaging. In one exemplary embodiment, the particle inspection can be performed by visual inspection, FTIR spectroscopy, Raman spectroscopy, or micro flow imaging (MF).

In some exemplary embodiments, the particle isolation 110 and particle capture 120 can be carried out using filtration devices.

In some exemplary embodiments, the chromatographic column 130 can be capable of being washed with a mobile phase. In one exemplary embodiment, the mobile phase can be ammonium acetate, ammonium bicarbonate, or ammonium formate, or combinations thereof.

In some exemplary embodiments, the mass spectrometer 140 can comprise a nanospray.

In some exemplary embodiments, the mass spectrometer 140 can be a tandem mass spectrometer. In one exemplary embodiment, the mass spectrometer 140 can be a tandem in space mass spectrometer. In one exemplary embodiment, the mass spectrometer 140 can be a tandem in time mass spectrometer.

Figure 8:
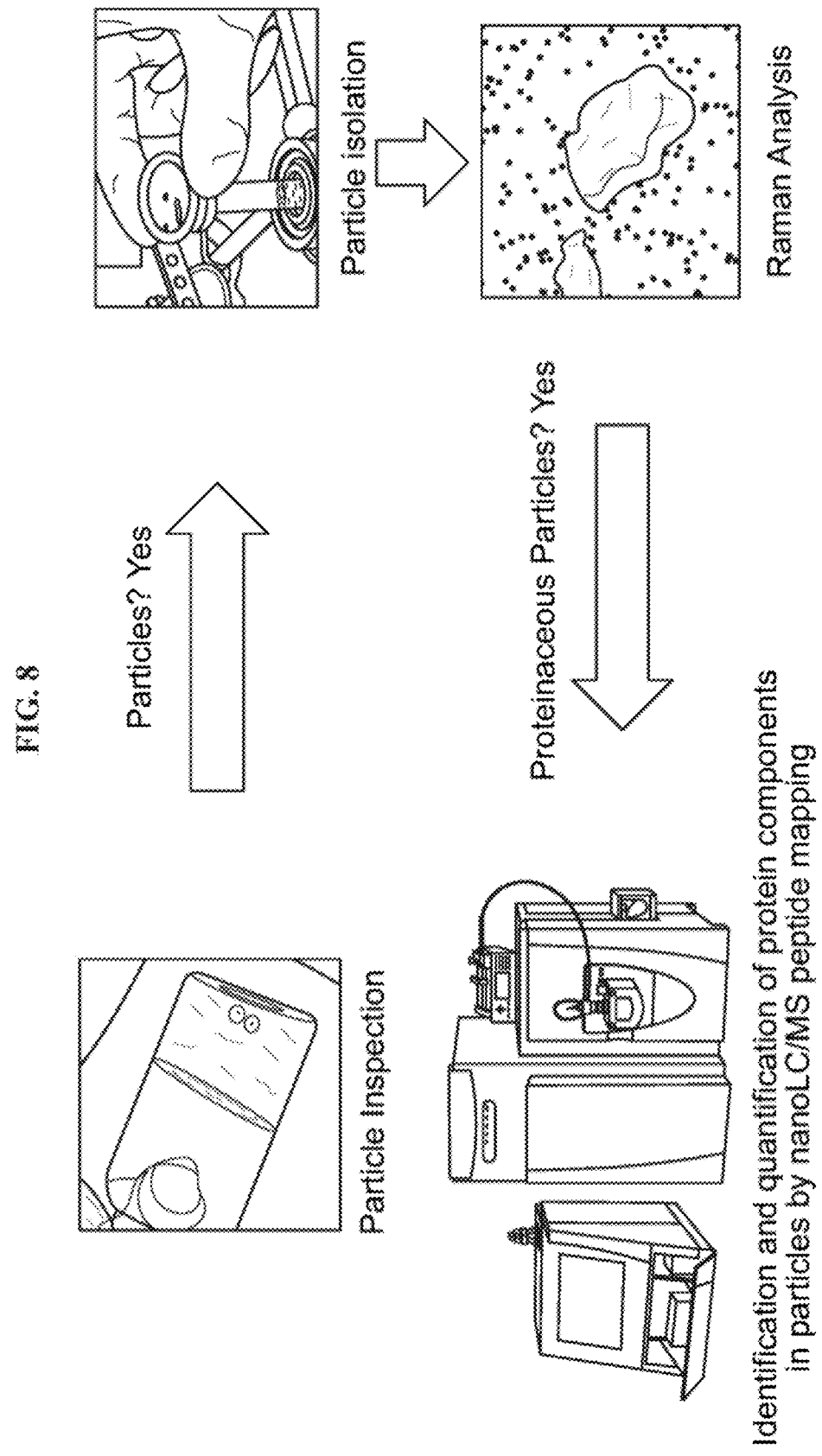
FIG. 8 shows a workflow for characterization of a protein or host-cell protein according to some exemplary embodiments.

An exemplary embodiment of the workflow in displayed in FIG. 8.

It is understood that the system is not limited to any of the aforesaid protein, host-cell protein, spectroscopy method, or chromatographic column.

The consecutive labeling of method steps as provided herein with numbers and/or letters is not meant to limit the method or any embodiments thereof to the particular indicated order.

Various publications, including patents, patent applications, published patent applications, accession numbers, technical articles and scholarly articles are cited throughout the specification. Each of these cited references is herein incorporated by reference, in its entirety and for all purposes.

The disclosure will be more fully understood by reference to the following Examples, which are provided to describe the disclosure in greater detail. They are intended to illustrate and should not be construed as limiting the scope of the disclosure.

EXAMPLES

Example 1

1.1 Detection of Particles

On evaluation of vials in a process performance qualification (PPQ) lot (lot no. 1) comprising mAb1 formulation, about 264 vials (~4.5%) of the PPQ lot had visible particles. Since, the acceptable limit for the PPQ lot is 0.7%, the lot was rejected.

The PPQ lot was evaluated for the presence of polysorbate level, which was found to be normal.

Figure 9:
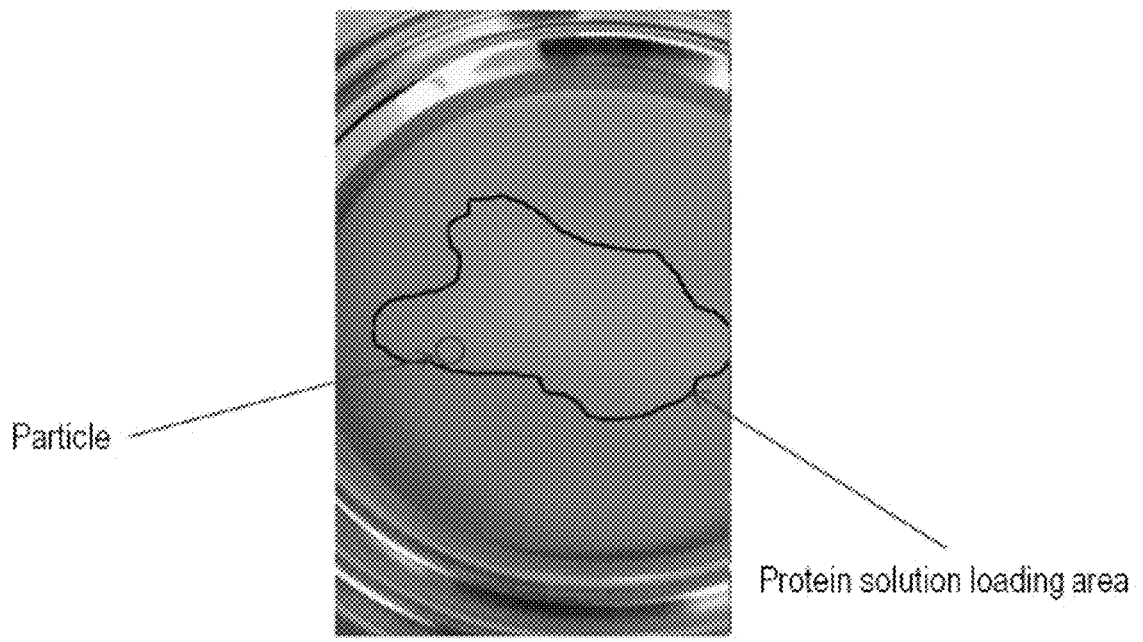
FIG. 9 shows a method of capturing a visible or sub-visible particle according to one exemplary embodiment.

A particle (particle 1) from the PPQ lot was captured on a grey filter (See FIG. 9).

1.2 Isolation of the Particle

Figure 10:
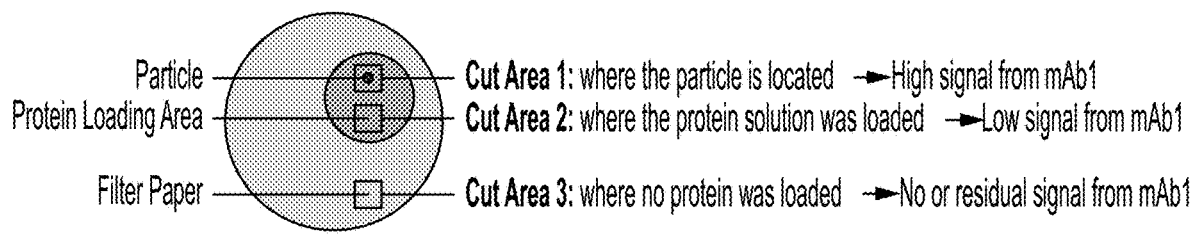
FIG. 10 shows excisions on filter paper made to evaluate a visible or sub-visible particle according to one exemplary embodiment.

Excisions were made on the filter paper: (a) cut area 1—a 4 mm×4 mm area where the particle 1 was loaded, (b) cut area 2—a 4 mm×4 mm area where the protein solution was loaded, and (c) cut are 3—a 4 mm×4 mm area where no protein was loaded (See FIG. 10). The cut areas/samples were dissolved in 8 M urea.

The samples were incubated with 8 M urea and 5 mM dithiothreitol (DTT) at 50° C. for 30 minutes, followed by incubation with 10 mM indole-3-acetic acid (IAA) at RT for 30 minutes. The incubate samples were digested with 1 μg of rLysC for 1 hour under denaturing condition, followed by dilution with Tris-HCl. To this mixture, 1 μg of trypsin was added and the digestion was continued for 3 hours. The digestion mixture was then acidified with 20% formic acid (FA) followed by nanoLC-MS/MS analysis.

1.3 Peptide Analysis

To find out the composition of particle 1, peptide analysis of particle 1 was carried out using nanoLC-MS/MS Thermo EASY-nLC coupled to Thermo QExactive HF mass spectrometer. The identity of the proteins present, the Proteome Discoverer v. 1.4 software using the Sequest mode was used by searching mass spectral data against a CHO protein sequence database. Peptide quality scores were derived by processing against a decoy database using the Peptide Validator node within Proteome Discoverer that calculates the probability that the search algorithm incorrectly included a peptide in a sample. The false discovery rate (FDR), or the false positive rate, is a statistical value that estimates the number of false positive identifications among all identifications found by a peptide identification search. Peptides assessed with less than 5% FDR (medium and high confidence peptides) were retained, and those assessed with less than a 1% FDR (high confidence) threshold noted as high confidence. A minimum of two medium or high confidence (passing) peptides per protein were required to positively identify each HCP. The MS/MS spectra of peptides for those proteins which were identified by only one high confidence peptide were manually examined for coverage of three or more consecutive b- and y-ions and low number of abundant extraneous ions to determine their acceptance.

Figure 11:
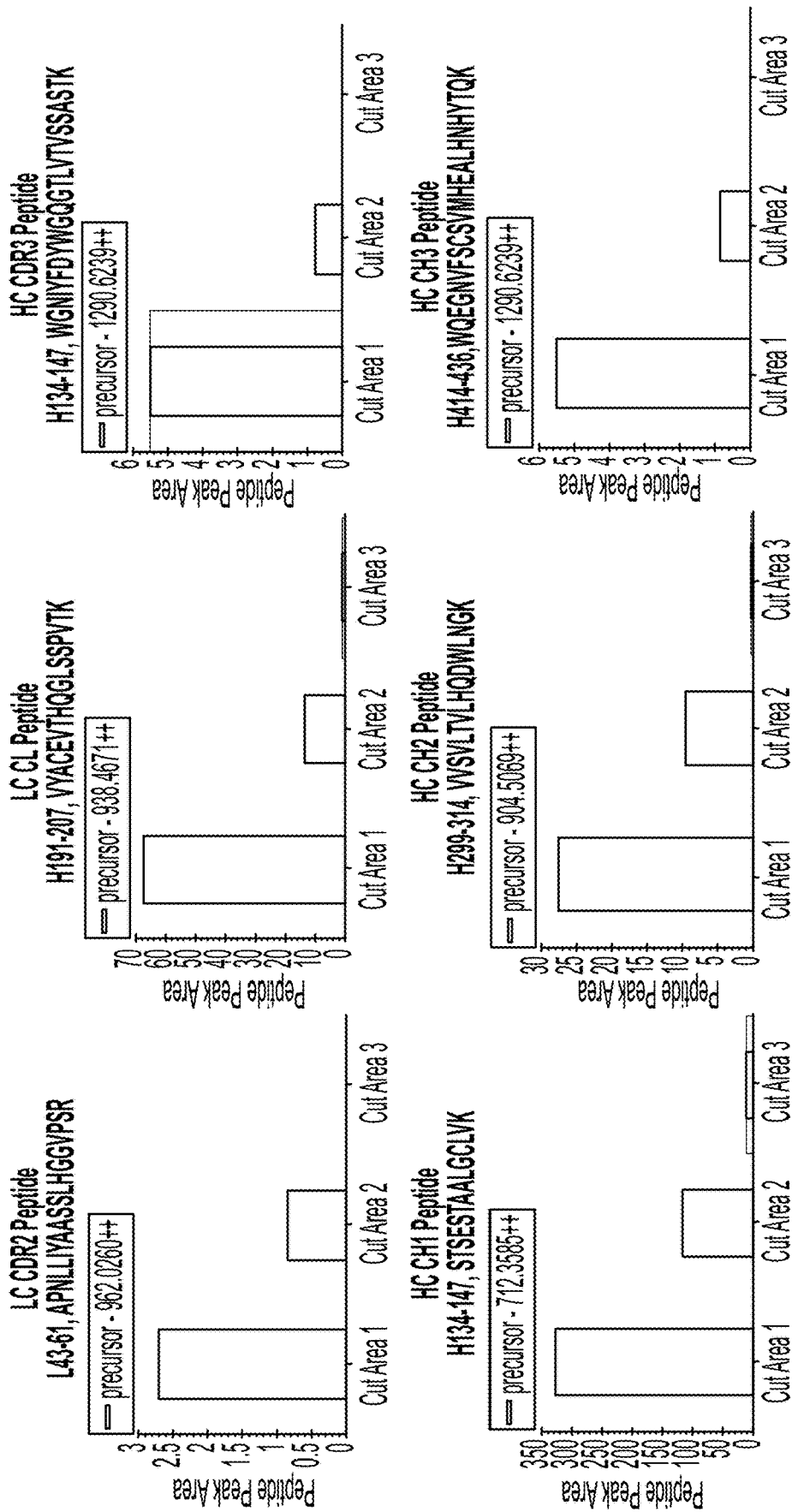
FIG. 11 shows comparisons of abundance of peptide fragments of mAb1 in cut areas of filter paper used to capture a visible or sub-visible particle according to an exemplary embodiment.

All the samples were analyzed for the abundance of mAb1. The cut area 1 (comprising particle 1) showed a high abundance of the mAb1 protein, followed by some presence of mAb1 in cut area 2 (protein solution without particle 1), and cut area 3 showed a low/absence of the mAb1 protein (See FIG. 11).

A host-cell protein other than mAb1—TIMP1 was found to be present in particle 1 (Table 1). However, TIMP1 was not present in the protein solution without particle 1 indicating that it was enriched in the particle.

TABLE 1

| Samples | Protein ID | Description | # of Unique Peptides Identified |
|---|---|---|---|
| Cut Area 1 (Particle) | mAb1 | HC | 37 |
| | mAb1 | LC | 22 |
| | TIMP1 | Metalloproteinase inhibitor 1 UniProt ID: P01033 | 4 |
| Cut Area 2 (Protein Loading) | mAb1 | HC | 31 |
| | mAb1 | LC | 16 |
| Cut Area 3 (Negative Control) | mAb1 | HC | 22 |
| | mAb1 | LC | 11 |

Example 2

Four additional particles (particles 2-5) were identified in the PPQ lot (lot no. 1) containing the formulation from mAb1. These particles were captured and analyzed.

2.1 Isolation of the Particle

Figure 12:
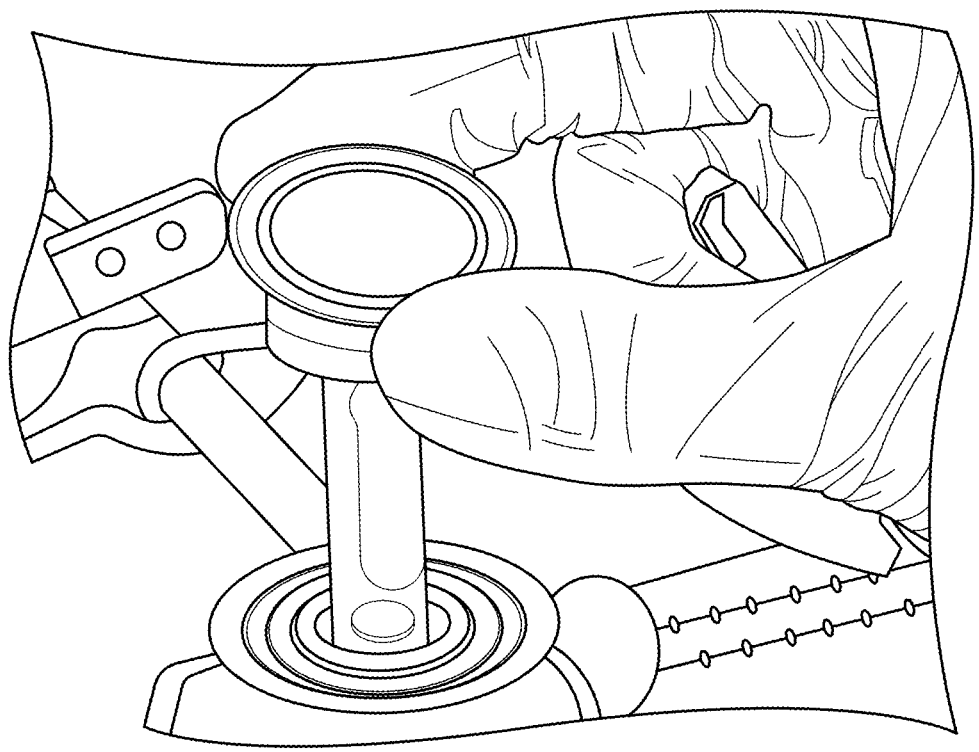
FIG. 12 shows a method of capturing a visible or sub-visible particle according on a gold-coated polycarbonate membrane to an exemplary embodiment.

Each detected particle was placed on an individual Rap ID gold-coated polycarbonate membrane with a pore size of 5 µM and 40/20 nm coating as shown in FIG. 12.

Excisions were made on the membranes to isolate the particle from the protein solution, as illustrated in example 1.

2.2 Raman Analysis

Figure 13:
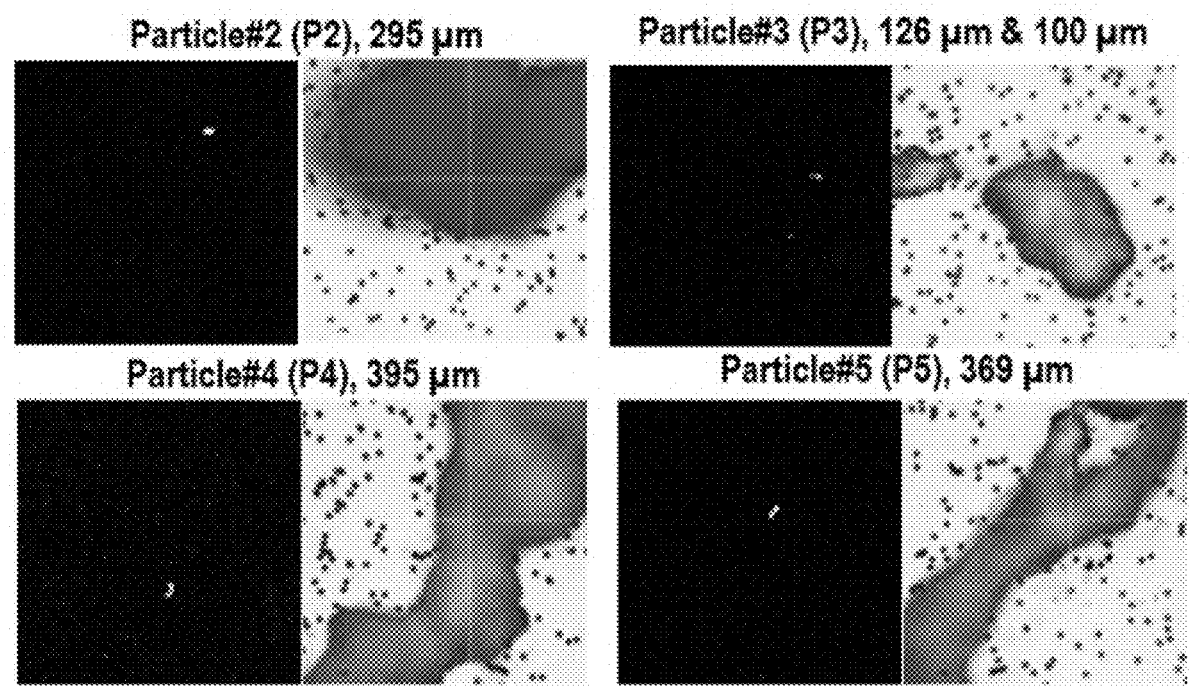
FIG. 13 shows a dark field illumination of particles analyzed using Raman spectroscopy isolated and captured according on a gold-coated polycarbonate membrane according to an exemplary embodiment.

Raman spectroscopy was employed to identify constituents of the particles. This method uses inelastic light scattering to generate an energy spectrum unique to each molecule, which is then compared to a reference library containing the fingerprints of various chemical structures. The Raman analysis confirmed that all four particles (particle 2, 3, 4 and 5) comprised protein. A dark field illumination showed that the particles surrounding areas has no or very minimal protein signals, which ensures that cutting particles form the filter did not induce contamination for MS analysis (See FIG. 13).

2.3 Peptide Analysis

To find out the composition of the particles, the peptide analysis of the particle was carried out using nanoLC-MS/MS as illustrated in example 1. Table 2 lists the host-cell proteins identified in particle 1 through 5, along with a drug solution lot (DS), all of which comprise mAb1. The host-cell proteins were screened using the regular nanoLC-MS/MS and confirmed using targeted nanoLC-MS/MS. Particles 3 and 4 were smaller in size and had about 10-50 times less protein amount that particle 1 and particle 5, which likely explains the result of less host-cell proteins being identified.

TABLE 2

| Protein | | Proteins identified | | | | | |
|---|---|---|---|---|---|---|---|
| ID | Description | DS | P1 | P2 | P3 | P4 | P5 |
| mAb1 | HC | Y | Y | Y | Y | Y | Y |
| mAb1 | LC | Y | Y | Y | Y | Y | Y |
| TIMP1 | Metalloproteinase inhibitor 1 UniProt ID: P01033 | N | Y | Y | N | N | Y |
| PPIB | Peptidyl-prolyl cis-trans isomerase B UniProt ID: P23284 | N | N | Y | N | N | Y |
| ITIH5 | Inter-alpha-trypsin inhibitor heavy chain H5 UniProt ID: Q86UX2 | N | N | Y | N | N | Y |
| PPIC | Peptidyl-prolyl cis-trans isomerase C UniProt ID: P45877 | N | N | Y | N | N | Y |
| ALDOA | Fructose-bisphosphate aldolase A UniProt ID: P04075 | N | N | Y | N | N | Y |
| ANXA1 | Annexin A1 UniProt ID: P04083 | N | N | Y | N | N | Y |
| CFL1 | Cofilin-1 UniProt ID: P23528 | N | N | Y | N | N | N |
| PTGR1 | Prostaglandin reductase 1 UniProt ID: F5GY50 | N | N | Y | N | N | N |
| CCL13 | C-C motif chemokine 13 UniProt ID: Q99616 | N | N | Y | N | N | Y |
| S100-A11 | Protein S100-A11 UniProt ID: P31949 | N | N | Y | N | N | N |

The study confirmed the presence of host-cell proteins in the particle isolated rejected mAb1 lot no. 1.

Example 3

To study if visible particles were enriched with host-cell proteins in other lots comprising mAb1 formulation, particles in a clinical lot comprising mAb1 formulation (lot no. 2) and two other PPQ lots comprising mAb1 formulation (lot nos. 3 and 4) lots were evaluated.

The isolation of particles, Raman analysis and peptide analysis was performed as illustrated in Example 2.

Table 3 lists the host-cell proteins identified in particles from lot no. 1 (a PPQ lot), lot no. 2 (a clinical lot), lot no. 3 (a PPQ lot), and lot no. 4 (a PPQ lot). The host-cell proteins were screened using the regular nanoLC-MS/MS and confirmed using targeted nanoLC-MS/MS. Some host-cell proteins were not identified in the initial screening but were identified using confirmatory assays. Particles in lot no. 2 (clinical lot) were smaller in size and had about 15-30 times less protein amount than particles from lot no. 4 (PPQ lot), which likely explains the result of less host-cell proteins being identified. Comparing the host-cell proteins identified to be present in the particles from these lots 2-4 suggests that the proteins identified in the visible particles isolated from the lot no. 1 are comparable.

TABLE 3

| Protein ID | Description | Identified Lot no. 1 | 2 | 3 | 4 | Confirmed Lot no. 1 | 2 | 3 | 4 |
|---|---|---|---|---|---|---|---|---|---|
| mAb1 | Heavy Chain | Y | Y | Y | Y | Y | Y | Y | Y |
| mAb1 | Light Chain | Y | Y | Y | Y | Y | Y | Y | Y |
| TIMP1 | Metalloproteinase inhibitor 1 UniProt ID: P01033 | Y | N | N | Y | Y | N | N | Y |
| PPIB | Peptidyl-prolyl cis-trans isomerase B UniProt ID: P23284 | Y | N | N | Y | Y | Y | N | Y |
| ITIH5 | Inter-alpha-trypsin inhibitor heavy chain H5 UniProt ID: Q86UX2 | Y | N | N | Y | Y | N | N | Y |
| PPIC | Peptidyl-prolyl cis-trans isomerase C UniProt ID: P45877 | Y | N | N | Y | Y | N | N | Y |
| ALDOA | Fructose-bisphosphate aldolase A UniProt ID: P04075 | Y | N | N | Y | Y | N | N | Y |
| ANXA1 | Annexin A1 UniProt ID: P04083 | Y | N | N | Y | Y | N | N | Y |
| CFL1 | Cofilin-1 UniProt ID: P23528 | Y | N | N | N | Y | N | N | Y |
| CCL13 | C-C motif chemokine 13 UniProt ID: Q99616 | Y | N | N | Y | Y | Y | N | Y |
| S100-A11 | Protein S100-A11 UniProt ID: P31949 | Y | N | N | N | Y | N | N | Y |
| ANXA2 | Annexin A2 UniProt ID: H0YMU9 | N | N | N | Y | — | Y | Y | Y |
| AK2 | Adenylate kinase 2, mitochondrial" UniProt ID: P54819 | N | N | N | Y | — | N | N | Y |
| ST3GAL1 | CMP-N-acetylneuraminate-beta-galactosamide-alpha-2,3-sialyltransferase 1" UniProt ID: Q11201 | N | N | N | Y | — | N | N | Y |
| GSTM2 | Glutathione S-transferase Mu 2 UniProt ID: P28161 | N | N | N | Y | — | N | N | Y |

Example 4

To study if drug solution of mAb1 which could make up the PPQ lots is enriched with host-cell proteins, drug solution lots (lot nos. 5-12) were evaluated.

4.1 PLBD2 Levels

The drug solution was tested for PLBD2 using LC-MS MRM method using Hamster putative phospholipase B-like 2 (PLBD2) ELISA kit, catalog CSB-EL018125Ha from CUSABIO. This kit claims to provide quantitative determination of hamster putative phospholipase B-like (PLBD2) concentrations. A standard curve was generated showing detection of the hamster PLBL2 standard included in the kit over the range of 0.12-8 ng/ml. Drug solution from lot nos. 5-12 demonstrated PLBD2 level below the lower limit of quantitation (1 ppm i.e., 1 ng of PLBD in 1 mg mAb1)

Thus, drug solution in all of the above lots showed absence of abnormal PLBD2 levels.

4.2 HCP Profiling Using Direct Peptide Mapping

Figure 14:
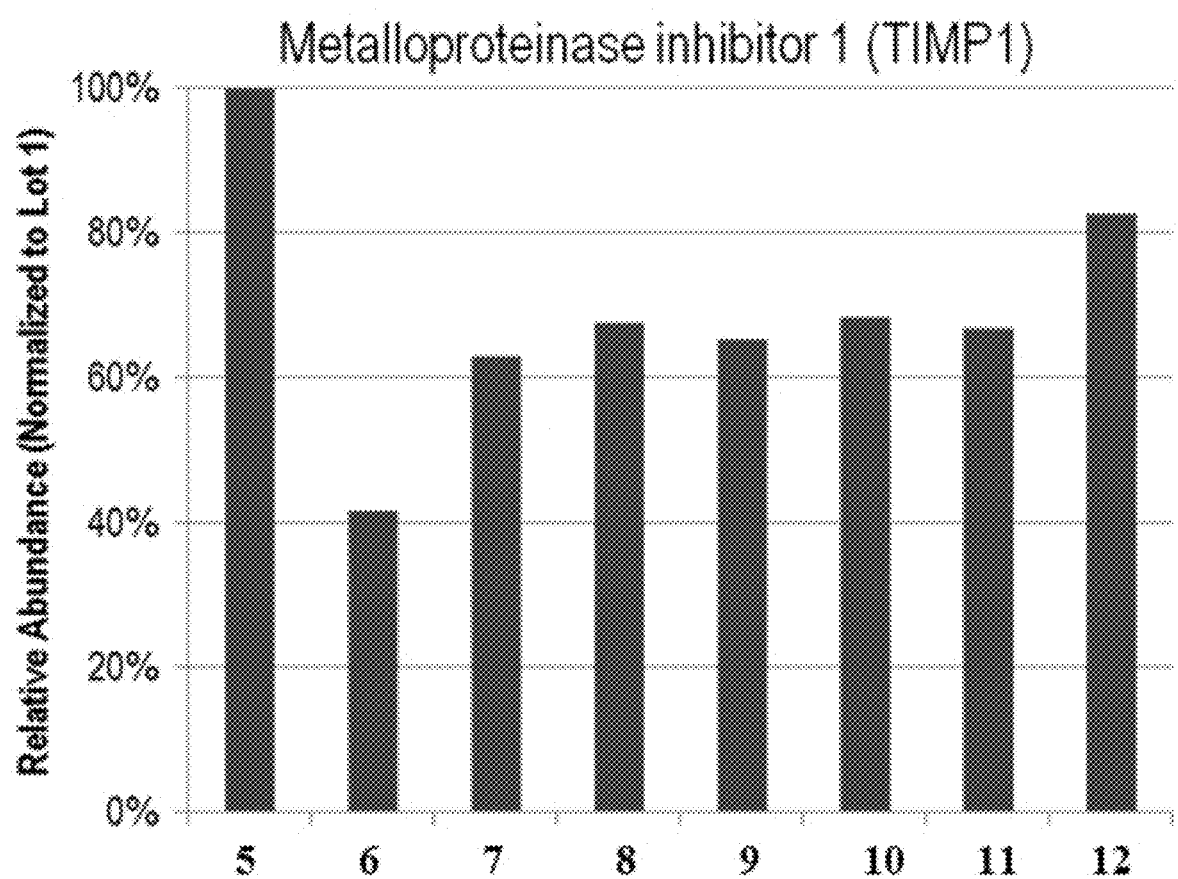
FIG. 14 shows the relative abundance of metalloproteinase inhibitor 1 (TIMP1) in drug solutions from different lots (lots 5-12) analyzed according an exemplary embodiment.
Figure 15:
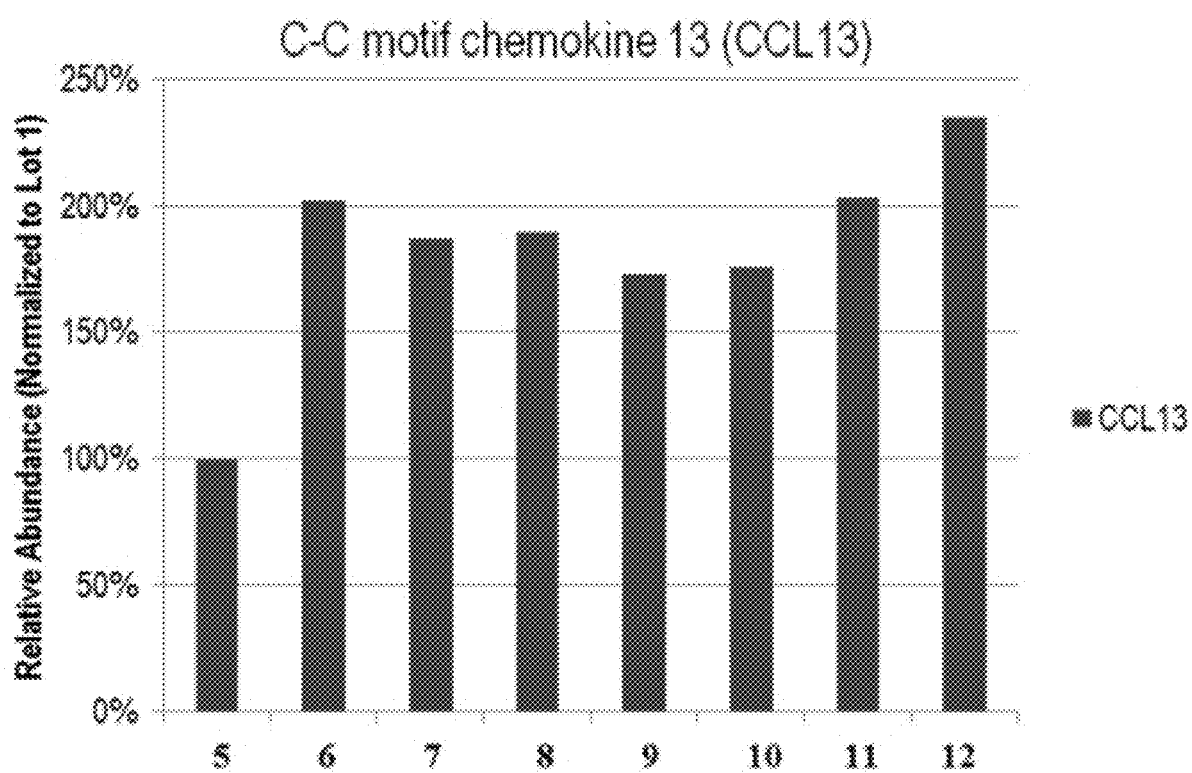
FIG. 15 shows the relative abundance of C-C motif chemokine 13 (CCL13) in drug solutions from different lots (lots 5-12) analyzed according an exemplary embodiment.

To find out the composition of the drug solution, peptide analysis was carried out using nanoLC-MS/MS as illustrated in example 1. The host-cell proteins were screened using the regular nanoLC-MS/MS and confirmed using targeted nanoLC-MS/MS. No host-cell proteins were identified in the any of the lots tested (lot nos. 5-12) (Table 4). TIMP1 and CCL13 were not identified in the initial screening of all the lots but were found to be present in the all the lots using more sensitive confirmatory assays. The relative abundance of the host cell proteins TIMP1 and CCL13 in drug solutions from lots 5-12 were plotted as normalized to relative abundance in lot no. 5 (See FIGS. 14 and 15).

Among the eight lots, lot no. 9 and lot no. 11 comprised drug solutions used to prepare the PPQ lots 1 and 3, respectively. The host cell proteins in the drug solutions in lot nos. 9 and 11 compared to the PPQ lots that they are used for suggests that there was not evaluated levels of host cell proteins observed in the lot that generated the particles compared to other drug substance lots.

TABLE 4

| Protein ID | Description | Identified proteins | Confirmed proteins |
|---|---|---|---|
| mAb1 | Heavy Chain | Detected | Detected |
| mAb1 | Light Chain | | |
| TIMP1 | Metalloproteinase inhibitor 1 UniProt ID: P01033 | Not Detected | Detected |
| CCL13 | C-C motif chemokine 13 UniProt ID: Q99616 | | |
| PPIB | Peptidyl-prolyl cis-trans isomerase B UniProt ID: P23284 | | Not Detected |
| ITIH5 | Inter-alpha-trypsin inhibitor heavy chain H5 UniProt ID: Q86UX2 | | |
| PPIC | Peptidyl-prolyl cis-trans isomerase C UniProt ID: P45877 | | |
| ALDOA | Fructose-bisphosphate aldolase A UniProt ID: P04075 | | |

TABLE 4-continued

| Protein ID | Description | Identified proteins | Confirmed proteins |
|---|---|---|---|
| ANXA1 | Annexin A1 UniProt ID: P04083 | | |
| CFL1 | Cofilin-1 UniProt ID: P23528 | | |
| PTGR1 | Prostaglandin reductase 1 UniProt ID: F5GY50 | | |
| S100-A11 | Protein S100-A11 UniProt ID: P31949 | | |
| ANXA2 | Annexin A2 UniProt ID: H0YMU9 | | |
| AK2 | Adenylate kinase 2, mitochondrial" UniProt ID: P54819 | | |
| ST3GAL1 | CMP-N-acetylneuraminate-beta-galactosamide-alpha-2,3-sialyltransferase 1" UniProt ID: Q11201 | | |
| GSTM2 | Glutathione S-transferase Mu 2 UniProt ID: P28161 | | |

4.3 HCP Profiling Using Anti-HCP Immunopurification (IP) Enrichment Followed by Peptide Mapping To further evaluate the host cell proteins present in the drug solution lots, a more sensitive anti-HCP immunopurification was carried out. A pool of biotinylated anti-HCP antibodies was used to pull-down and enriched HCPs by removing the therapeutic proteins and other components. Following the enrichment, the CPs were then digested by enzyme and injected on NanoLC-MS for HCP identification and quantification. The enrichment allows us to more sensitively identify and quantify HCPs.

Table 5 lists the host cell proteins which were identified by performing HCP profiling using anti-HCP immunopurification enrichment.

TABLE 5

| Gene ID | Protein | # of peptide spectrum matches for each lot | | | | | | | | MW [kDa] | calc. pI |
|---|---|---|---|---|---|---|---|---|---|---|---|
| | | 5 | 6 | 7 | 8 | 9 | 10 | 11 | 12 | | |
| TIMP1 | Metalloproteinase inhibitor 1 | 33 | 23 | 28 | 28 | 37 | 25 | 32 | 35 | 22.4 | 8.47 |
| GSTM6 | Glutathione S-transferase Mu 6 | 19 | 15 | 28 | 23 | 31 | 24 | 20 | 22 | 86.5 | 8.21 |
| PPIB | Peptidyl-prolyl cis-trans isomerase B | 9 | 7 | 10 | 5 | 8 | 3 | 5 | 4 | 23.6 | 9.58 |
| ITIH5 | Inter-alpha-trypsin inhibitor heavy chain H5 | 5 | 3 | 5 | 8 | 7 | 2 | 7 | 4 | 102.0 | 8.60 |
| CCL13 | C-C motif chemokine | 6 | 5 | 5 | 5 | 5 | 0 | 5 | 7 | 15.8 | 9.16 |
| PRDX1 | Peroxiredoxin-1 | 3 | 0 | 6 | 9 | 2 | 5 | 7 | 6 | 22.2 | 7.72 |
| ANXA1 | Annexin A1 | 4 | 0 | 6 | 4 | 3 | 2 | 0 | 0 | 38.8 | 7.02 |
| CXCL3 | C-X-C motif chemokine | 4 | 0 | 4 | 2 | 3 | 0 | 0 | 2 | 11.0 | 8.81 |
| GSTP1 | Glutathione S-transferase P | 2 | 4 | 2 | 2 | 5 | 0 | 0 | 0 | 25.0 | 8.12 |
| DDT | D-dopachrome decarboxylase | 2 | 2 | 3 | 2 | 2 | 0 | 0 | 2 | 13.1 | 7.14 |
| CTSZ | Cathepsin Z | 0 | 2 | 2 | 3 | 2 | 0 | 0 | 3 | 34.0 | 7.58 |
| SIAE | Sialate O-acetylesterase | 0 | 0 | 3 | 3 | 2 | 0 | 0 | 2 | 61.4 | 8.22 |
| B2M | Beta-2-microglobulin | 0 | 0 | 0 | 0 | 3 | 0 | 0 | 4 | 6.39 | 5.81 |
| C1RA | Complement C1r-A subcomponent | 2 | 0 | 3 | 0 | 0 | 0 | 0 | 0 | 80.05 | 6.06 |
| CTSL | Cathepsin L1 | 0 | 0 | 2 | 0 | 0 | 0 | 2 | 0 | 37.22 | 7.17 |

Comparing the host cell proteins identified in lot no. 1 (PPQ lot, Table 5) to lot no. 9 (drug solution lot used to prepare the lot no. 1, Table 3), it can be concluded that no unique host cell protein is associated with the lot no. 1. This suggests that the host cell protein profile in the PPQ lot was similar to the host cell protein profile in the drug solution lot.

Example 5

The host-cell proteins could be enriched as a consequence of aggregate formation. This was studied by comparing the host-cell proteins in drug solution lot (lot no. 6) with lots enriched with high molecular weight species of mAb1 as represented in table 6 below.

TABLE 6

| Lot no. | Sample Description |
|---|---|
| 6 | DS control with mAb1 |
| 13 | Total HMW (contains 93% total HMW material of mAb1) |
| 14 | Dimer (contains 90% dimer of mAb1) |
| 15 | vHMW (contains 92% vHMW material of mAb1) |

The isolation of particles and Raman analysis for lots 13-15 was performed as illustrated in Example 2.

5.1 Host Cell Proteins Identified Using Direct Peptide Mapping

The samples were dried down using SpeedVac, and then dissolved by 8M Urea and 10 mM TCEP-HCl, and denatured at 50° C. for 30 minutes, followed by incubation with 10 mM indole-3-acetic acid (IAA) at RT for 30 minutes. The incubate samples were digested with 1 μg of rLysC for 1 hour under denaturing condition, followed by dilution with Tris-HCl. To this mixture, 1 μg of trypsin was added and the digestion was continued for 3 hours. The digestion mixture was then acidified with 20% formic acid (FA) followed by nanoLC-MS/MS analysis. Six host cell proteins were identified in the lot with enriched HMW mAb1 species, but not in the drug solution lot (Table 7).

TABLE 7

| | | Identified in the lot | | | |
|---|---|---|---|---|---|
| Protein ID | Description | 6 | 13 | 14 | 15 |
| TIMP1 | Metalloproteinase inhibitor 1 | | Yes | Yes | |
| OST-Mu 7 | Glutathione S-Transferase Mu7 | | Yes | | |
| PRDX1 | Peroxiredoxin | | Yes | Yes | |
| LDH | L-lactate dehydrogenase | | | | Yes |
| ANXA1 | Annexin A1 | | Yes | | |
| H2A | Histone H2A Type 1 | | | Yes | |

5.2 Relative Quantitation of Host Cell Proteins Using Targeted LC-MS/MS

Figure 16:
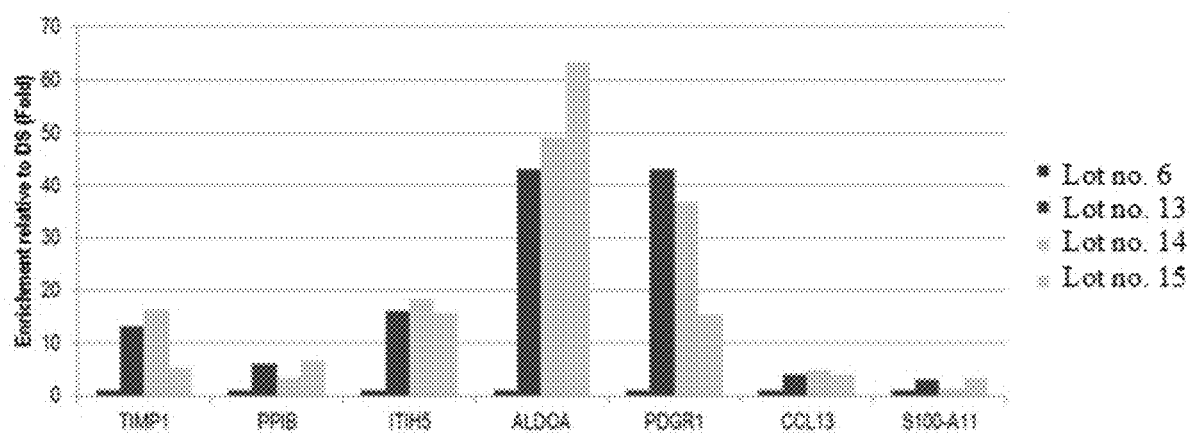
FIG. 16 shows the relative quantitation of host-cell proteins identified in high molecular weight samples using targeted LC-MS/MS according to an exemplary embodiment.

The identified peptide/protein from Step 5.1 above was used to create a mass list of identified peptides in order for the mass spectrometer to look for these specific peptides to fragment to further confirm and quantify the HCPs. In doing so, the detection sensitivity was increased due to the targeted screening. Seven host cell proteins were identified in the lots with enriched HMW mAb1 species (lot nos. 13-15). The amount of the host cell proteins identified in the lots with enriched HMW mAb1 species was about 2-60 fold higher than the amount of the host cell proteins in the drug solution lot (lot no. 6). FIG. 16 shows a chart of relative quantitation of host cell proteins in the lots with enriched HMW mAb1 species.

5.3 Host Cell Proteins Identified Using Anti-HCP IP Enrichment Followed by Peptide Mapping A pool of biotinylated anti-HCP antibodies was used to pull-down and enriched HCPs by removing the therapeutic proteins and other components. Following the enrichment, the HCPs were then digested by enzyme and injected on NanoLC-MS for HCP identification and quantification. Thirty one host cell proteins were identified in the lots with enriched HMW mAb1 species (lot nos. 13-15). Out of thirty one host cell proteins, the drug solution lot only showed the presence of two host cell proteins (Table 8).

TABLE 8

| # | Accession | Protein Name | # of peptide spectrum matches for each mAb1 lot | | | | MW [kDa] | calc. pI |
|---|---|---|---|---|---|---|---|---|
| | | | 6 | 13 | 14 | 15 | | |
| 1 | G3IBH0 | Metalloproteinase inhibitor 1 | 13 | 74 | 74 | 23 | 22.39 | 8.47 |
| 2 | G3IKC3 | Glutathione S-transferase Mu 6 | 10 | 75 | 69 | 30 | 86.50 | 8.21 |
| 3 | G3HXN7 | Beta-hexosaminidase | 0 | 70 | 83 | 14 | 60.06 | 7.36 |
| 4 | G3ILF3 | Glutathione S-transferase Mu 7 | 0 | 22 | 26 | 0 | 25.86 | 7.37 |
| 5 | G3GYP9 | Peroxiredoxin-1 | 0 | 15 | 15 | 7 | 22.22 | 7.72 |
| 6 | G3IIB1 | Sialate O-acetylesterase | 0 | 8 | 16 | 0 | 61.38 | 8.22 |
| 7 | G3I5L3 | Annexin A1 | 0 | 11 | 6 | 2 | 38.84 | 7.02 |
| 8 | G3I5Z5 | Prostaglandin reductase 1 | 0 | 9 | 8 | 0 | 42.59 | 6.27 |
| 9 | G3H533 | Peptidyl-prolyl cis-trans isomerase | 0 | 6 | 5 | 0 | 23.62 | 9.58 |
| 10 | G3I6T1 | Putative phospholipase B-like 2 | 0 | 0 | 10 | 4 | 65.50 | 6.28 |
| 11 | G3INC5 | Cathepsin L1 | 0 | 7 | 5 | 0 | 37.22 | 7.17 |
| 12 | G3HYO3 | D-dopachrome decarboxylase | 0 | 6 | 5 | 0 | 13.12 | 7.14 |
| 13 | G3GTT2 | C-C motif chemokine | 0 | 7 | 3 | 0 | 15.85 | 9.16 |
| 14 | G3I3K5 | G-protein coupled receptor 56 | 0 | 7 | 2 | 0 | 77.32 | 8.82 |
| 15 | G3GUR1 | Complement C1r-A subcomponent | 0 | 3 | 5 | 0 | 80.05 | 6.06 |
| 16 | G3IEU2 | Protein DJ-1 | 0 | 4 | 3 | 0 | 19.92 | 6.79 |
| 17 | G3HCL3 | Tumor necrosis factor ligand superfamily member 9 | 0 | 3 | 3 | 0 | 33.63 | 6.24 |
| 18 | G3I3V6 | Discoidin, CUB and LCCL domain-containing protein 2 | 0 | 2 | 3 | 0 | 73.60 | 7.49 |
| 19 | G3GRS9 | N-acetylgalactosamine-6-sulfatase | 0 | 3 | 3 | 0 | 53.99 | 6.93 |
| 20 | G3I664 | Procollagen C-endopeptidase enhancer 1 | 0 | 4 | 0 | 0 | 55.19 | 8.13 |

TABLE 8-continued

|  |  |  | # of peptide spectrum matches for each mAb1 lot | | | | MW | calc. |
|---|---|---|---|---|---|---|---|---|
| # | Accession | Protein Name | 6 | 13 | 14 | 15 | [kDa] | pI |
| 21 | G3HDU7 | Histone H4 | 0 | 2 | 0 | 2 | 10.82 | 11.50 |
| 22 | G3I255 | L-lactate dehydrogenase | 0 | 3 | 0 | 0 | 42.15 | 8.43 |
| 23 | G3GZZ0 | Aspartate aminotransferase | 0 | 3 | 0 | 0 | 46.22 | 7.21 |
| 24 | G3H0S7 | Beta-2-microglobulin | 0 | 2 | 1 | 0 | 6.39 | 5.81 |
| 25 | G3H8V4 | Phospholipid transfer protein | 0 | 3 | 0 | 0 | 54.34 | 6.65 |
| 26 | G3GS02 | 10-formyltetrahydrofolate dehydrogenase | 0 | 0 | 0 | 2 | 96.16 | 5.90 |
| 27 | G3HNJ3 | Clusterin | 0 | 0 | 0 | 0 | 51.72 | 5.74 |
| 28 | G3HGM6 | N(4)-(Beta-N-acetylglucosaminyl)-L-asparaginase | 0 | 0 | 2 | 0 | 37.21 | 7.46 |
| 29 | G3H8V5 | Carboxypeptidase | 0 | 0 | 1 | 0 | 54.19 | 6.11 |
| 30 | G3HCX3 | Deoxyribonuclease-2-alpha | 0 | 1 | 0 | 0 | 40.38 | 7.55 |
| 31 | G3I3Y6 | Glutathione S-transferase P | 0 | 1 | 0 | 0 | 24.98 | 8.12 |

The above results show a higher amount and enrichment of host cell proteins in lots with HMW mAb1 species than mAb1 drug solution lot. This suggests that host cell proteins are enriched HMW mAb1 species.

Example 6

Drug product comprising mAb1 was also tested for the presence of visible particles and host cell proteins, in addition to testing drug solution of mAb1, lot comprising HMW species of mAb1 and PPQ lots of mAb1.

6.1 Detection of Particles

Two vials (vial #1 and vial #2) comprising the drug product—containing a mAb1 was inspected manually to detect the presence of a particle(s).

6.2 Isolation of the Particle

Figure 17:
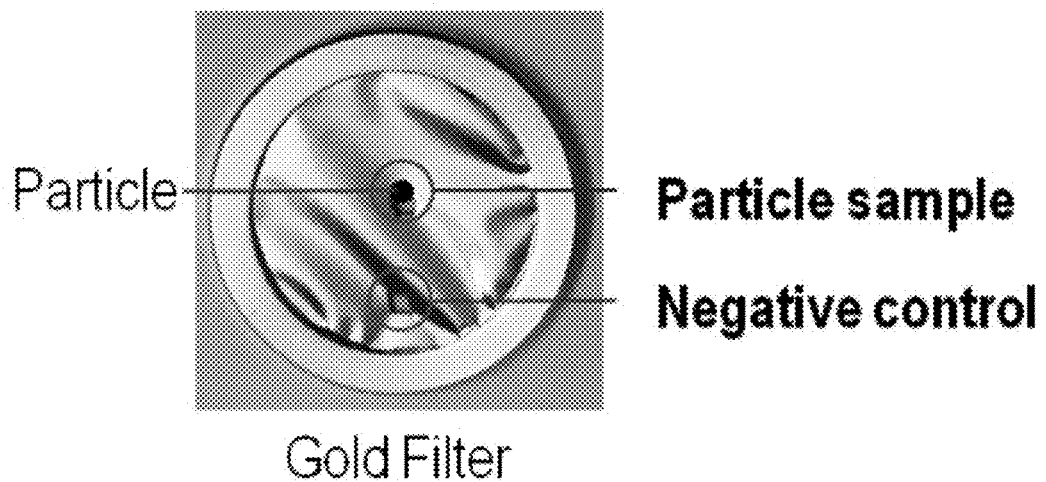
FIG. 17 shows a method of capturing a visible or sub-visible particle according on a gold-filter according to an exemplary embodiment.

For each of the vial, the detected particle was placed on an individual (Rap ID) gold-coated polycarbonate membrane with a pore size of 5 μM and 40/20 nm coating as shown in FIG. 17.

Figure 18:
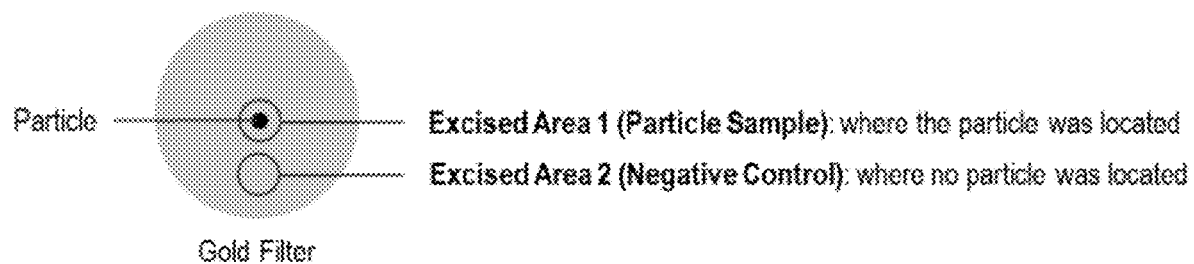
FIG. 18 shows a method of isolating a visible or sub-visible particle on a gold-filter according to an exemplary embodiment.

Excisions were made on the membranes: (a) particle sample—a 3 mm diameter circular area with the particle(s) was excised and (b) negative control—a 3 mm diameter circular area without the particle was excised (FIG. 18). The particle sample and negative sample were dissolved in 8 M urea. Three particle samples and two negative controls were isolated from the membranes for the two vials as represented in Table 9.

TABLE 9

| Source Vial# | Gold Filter# | Samples |
|---|---|---|
| Vial#1 | Filter#1 | Filter#1 Particle#1 |
|  |  | Filter#1 Control |
| Vial#2 | Filter#2 | Filter#2 Particle#1 |
|  |  | Filter#2 Particle#2 |
|  |  | Filter#2 Control |

6.3 Raman Analysis

Figure 19:
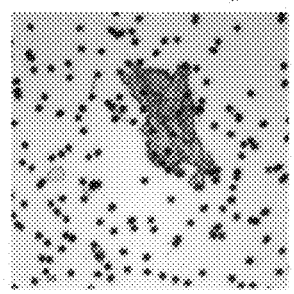
FIG. 19 shows the confirmation of presence of protein in a visible or sub-visible particle using Raman spectroscopy according to an exemplary embodiment.
Figure 19:
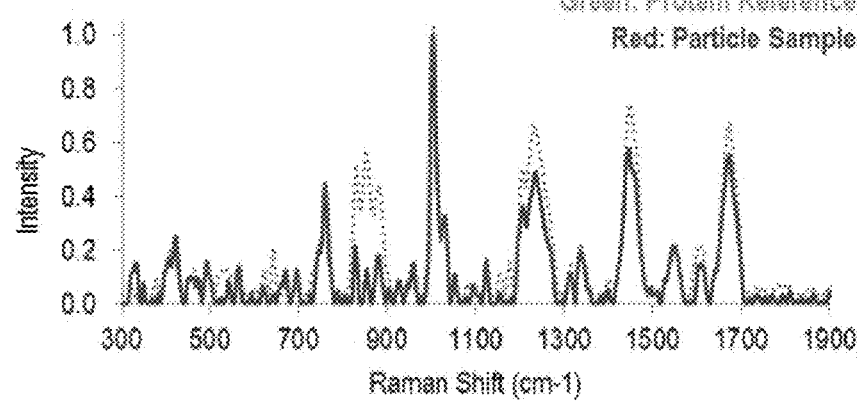

Raman spectroscopy was performed on the particles as illustrated in example 2. The Raman spectra of one of the particle 1 as recited in table 9 confirmed that the particles were proteinaceous (See FIG. 19). The green trace as seen in FIG. 19 is the protein reference spectrum and the red trace as seen in FIG. 19 is the particle sample spectrum.

6.4 Peptide Analysis

Peptide analysis was performed on the particles as illustrated in example 2.

Figure 20:
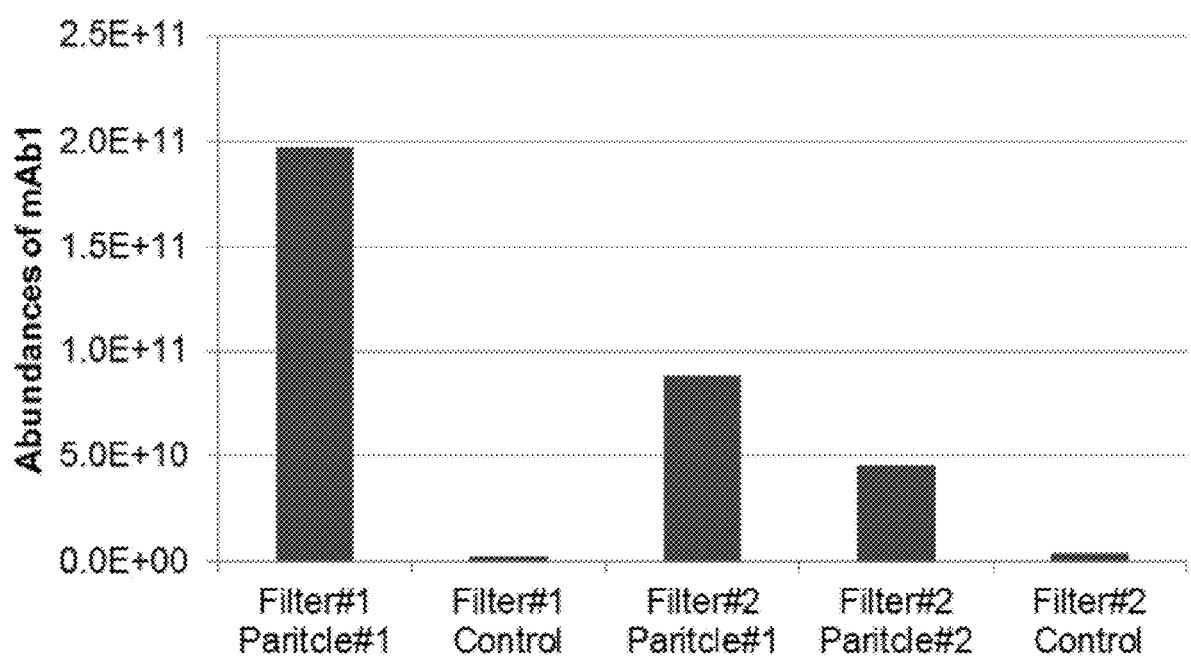
FIG. 20 shows the abundance of mAb1 in particles characterized according to an exemplary embodiment.

All the particle samples and negative samples were analyzed for the abundance of mAb1. The particle samples showed a high abundance of the mAb1 protein and negative samples showed absence of the mAb1 protein (See FIG. 20). The abundance peaks were estimated based on the averaged peak areas of the top 2 most abundant peptides in mAb1.

Proteins other than mAb1 obtained from the peptide analysis are represented in table 10.

The mAb1 abundance in the particle samples and negative samples was normalized to 1 E6 to relatively quantify the other proteins in ppm in Table 10. The term ND in table 10 is to represent that the protein was not detected.

TABLE 10

| | Abundances of HCP relative to DS in each sample (ppm) | | | | |
|---|---|---|---|---|---|
| Protein | Vial#1 (Filter#1) | | Vial#2/Filter#2 | | |
| ID | Paritcle#1 | Control | Paritele#1 | Paritcle#2 | Control |
| mAb1 | 1E6 | 1E6 | 1E6 | 1E6 | 1E6 |
| G3IBH0 | 1229 | ND | 366 | 328 | ND |
| G3I4H6/ A0A061IB69 | 115 | ND | 81 | 93 | ND |
| G3I5L3/ A0A061I6Z5 | 60 | ND | ND | ND | ND |
| G3H533 | 339 | ND | ND | ND | ND |
| G3HKB0 | 90 | ND | ND | ND | ND |
| G3H928 | 169 | ND | ND | ND | ND |
| G3ILF3 | 83 | ND | ND | ND | ND |
| G3GTT2 | ND[2] | ND | 62 | ND | ND |

The presence of protein in the particle samples and negative samples is shown in table 11.

TABLE 11

| | Particle Samples | | | Negative Controls | |
|---|---|---|---|---|---|
| UniProt ID | Filter#1 Paritcle#1 | Filter#2 Paritcle#1 | Filter#2 Paritcle#2 | Filter#1 Control | Filter#2 Control |
| mAb1 | Y | Y | Y | Y | Y |
| G3IBH0 | Y | Y | Y | | |
| G3I4H6/ A0A061IB69 | Y | Y | Y | | |
| G3I5L3/ A0A061I6Z5 | Y | | | | |
| G3H533 | Y | Y | | | |
| G3HKB0 | Y | Y | | | |

TABLE 11-continued

|  | Particle Samples | | | Negative Controls | |
| --- | --- | --- | --- | --- | --- |
| UniProt ID | Filter#1 Paritcle#1 | Filter#2 Paritcle#1 | Filter#2 Paritcle#2 | Filter#1 Control | Filter#2 Control |
| G3H928 | Y | | | | |
| G3ILF3 | Y | | | | |
| G3GTT2 | | | Y | | |

The peptide analysis revealed the presence of host-cell proteins in the particle isolated from drug product containing mAb1.

Example 7

Detection of sub-visible particles was also performed using a Formulated Drug Substance (FDS) comprising mAb1.

In order to isolate sub-visible particles, 1.5 ml of the FDS solution was pipetted on a gold-coated polycarbonate membrane with a pore size of 5 µM and 40/20 nm coating. This was then washed with milli-Q water. A particle free negative control was established for comparison by initially pipetting 1.5 ml of the FDS solution on a 0.2 µM filter (Millipore) and the flow-through was collected. The flow-through was then pipetted on a gold-coated polycarbonate membrane with a pore size of 5 µM and 40/20 nm coating and washed with milli-Q water.

Figure 21:
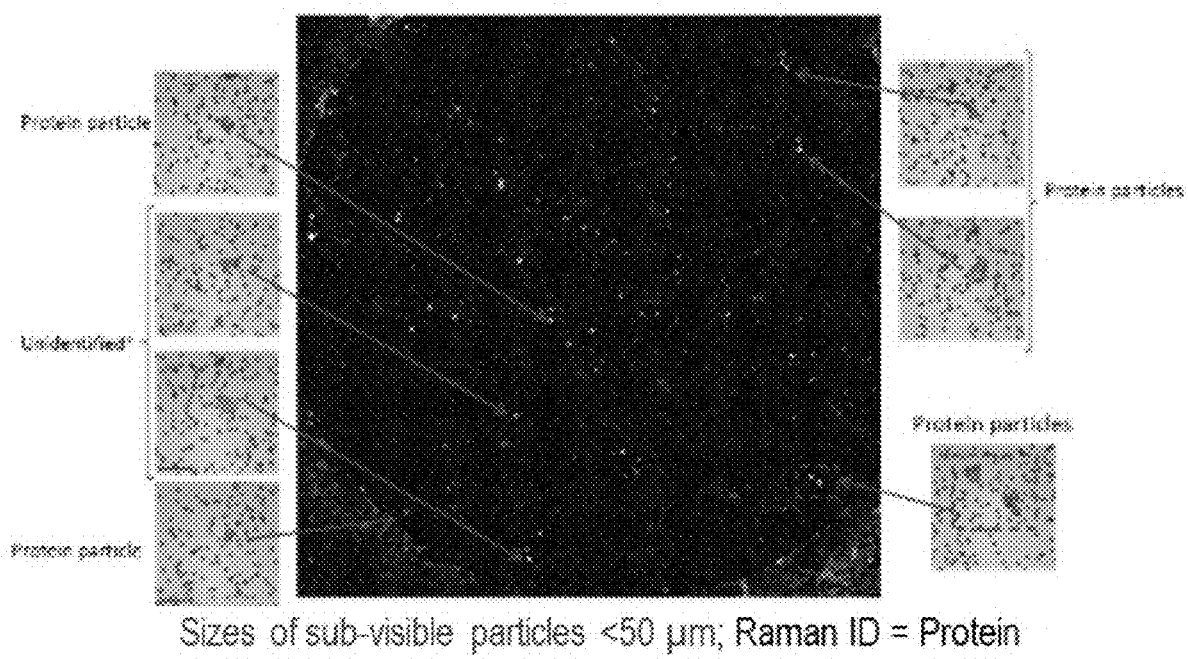
FIG. 21 shows a dark-filled image of a sample comprising sub-visible particles taken according to an exemplary embodiment.

Raman analysis and peptide analysis was performed as described in Example 2. The particles comprising protein were identified using the Raman spectroscopy. The dark-filled images of the particles comprising proteins identified by the recited method is shown in FIG. 21. The peptide analysis of the sub-visible particles demonstrated the presence of a host cell protein—Metalloproteinase inhibitor 1 along with mAb1, whereas the particle free negative control showed only the presence of mAb1. The absence of the host protein Metalloproteinase inhibitor 1 in the particle free negative control suggests that the host cell proteins were enriched in the sub-visible particles only (Table 12).

| | | Detected by nanoLC-MS/MS | |
| --- | --- | --- | --- |
| Protein ID | Description | Sub-Visible Particles | Particle-Free Negative Control |
| mAb1 | Heavy Chain | Yes | Yes |
| mAb1 | Light Chain | Yes | Yes |
| TIMP1 | Metalloproteinase inhibitor 1 UniProt ID: P01033 | Yes | No |

Example 8

To evaluate the presence of host cell proteins in bioprocess, harvested cell culture fluid (HCCF) from Preclinical Manufacturing and Process Development (PMPD) for mAb2 was tested. The HCCF for mAb2 showed presence of particles after sterile filtration and on freeze-thaw cycle. During the HCCF sterilizing filtration step at Industrial Operations and Product Supply (IOPS), high back pressure was experiences, indicating some non-soluble materials were clogging the filter.

Figure 22:
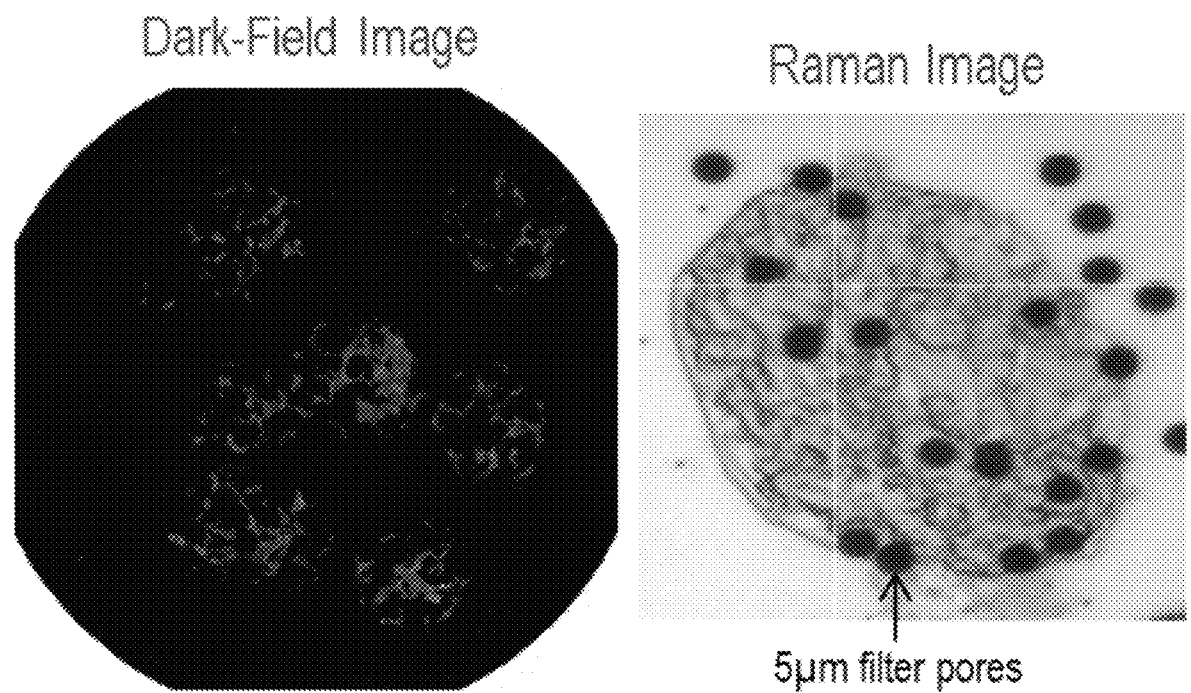
FIG. 22 shows a dark-filled image and Raman image of a sample comprising sub-visible particles taken according to an exemplary embodiment.

The isolation of particles, Raman analysis and peptide analysis was performed as illustrated in Example 2. FIG. 22 shows a dark filled image and a Raman image of the particles. Other than mAb2, 743 host cell proteins were identified in one of the particles. The top ten HCPs (based on sequence coverage) were L-lactate dehydrogenase (UniProt Accession: Q06BU8), Actin, cytoplasmic (UniProt Accession: G3GVD0), Transketolase (UniProt Accession: G3GUU5), Rab GDP dissociation inhibitor beta (UniProt Accession: G3GR73), Glyceraldehyde-3-phosphate dehydrogenase (UniProt Accession: P17244), V-type proton ATPase catalytic subunit A (UniProt Accession: G3H066), Transgelin (UniProt Accession: G3H7Z2), Glutathione S-transferase Mu 5 (UniProt Accession: G3ILF1), Chloride intracellular channel protein 4 (UniProt Accession: G3HMU4), and Leukotriene A-4 hydrolase (UniProt Accession: G3HBI9).

Example 9

Particles comprised of host cell proteins at different steps in bioprocess can be lead to decrease in filter capacity. To assess the presence of host cell proteins in bioprocess, cell culture fluid (CCF) for mAb3/mAb2 bioprocess was tested.

9.1 Filter Capacity Assessment

The PMPD and the IOPS processes exhibited an abnormally low CCF filtration throughput in a few lots from various programs. For the one of the mAb3/mAb2 lot, harvest pool filter capacity was assessed after incubated for 0, 24, 48, and 72 hours at room temperature. The filter capacity assessment was performed using the Vmax method on the CCF filter pool at the above mentioned time points (Vmax™ Constant Pressure Test Protocol, Merck Millipore). In the Vmax™ test, the time and volume collected up to that time were recorded at regular intervals. The data was then plotted as time/volume versus time.

Figure 23:
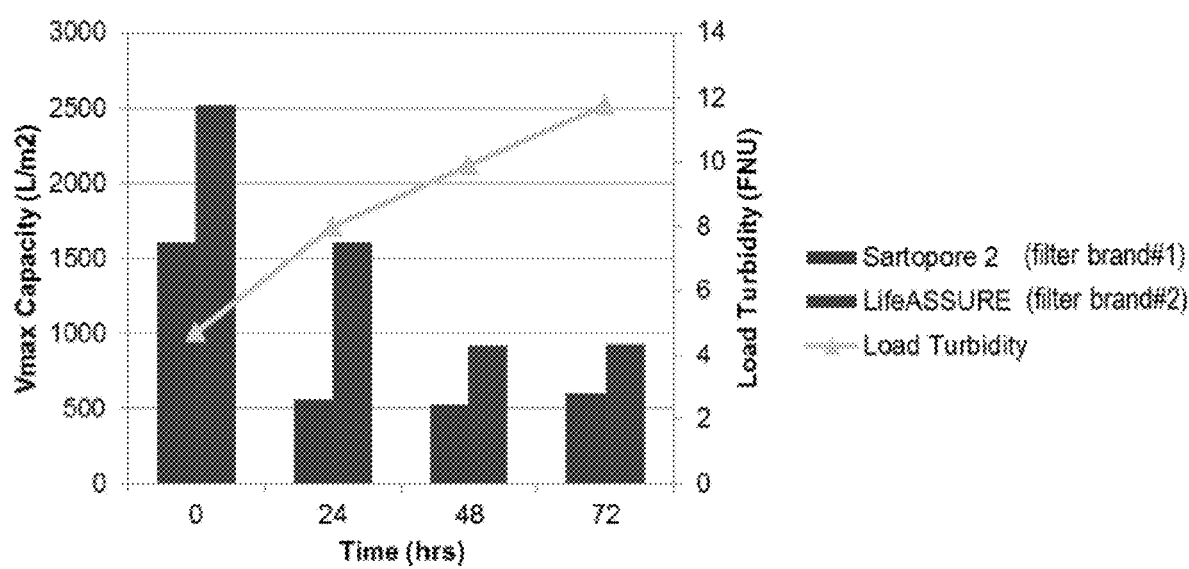
FIG. 23 shows a graph of decrease in Vmax capacity and turbidity over time for two filters used to characterize particles according to an exemplary embodiment.

Two types of filters were used for the assessment—Sartopore® 2 (two layers of filters with 0.45 µm and 0.2 µm, respectively.) and LifeASSURE™ (two layers of filters with 0.65 µm and 0.2 µm, respectively)). The plot of Vmax capacity (L/m$^2$) vs. time in hours (See FIG. 23) showed a decrease in Vmax™ over time, indicating aggregation or particle formation over time. The increase in time also showed an increase in turbidity. This increase in turbidity and decrease in filter capacity could be due to precipitation of host cell proteins or drug solution over time clogging the filters.

9.2 Protein Abundance Quantitation

To find out the cause of the increase in turbidity and decrease in filter capacity, CCF for mAb2 (pI: ~6.3) was incubated pre-filtration for 0, 24, 48 and 72 hours at pH 5.60-6.10. The incubated CCF fluid at each time points was filtered using LifeASSURE™ filter (two layers of filters with 0.65 µm and 0.2 µm, respectively).

Figure 24:
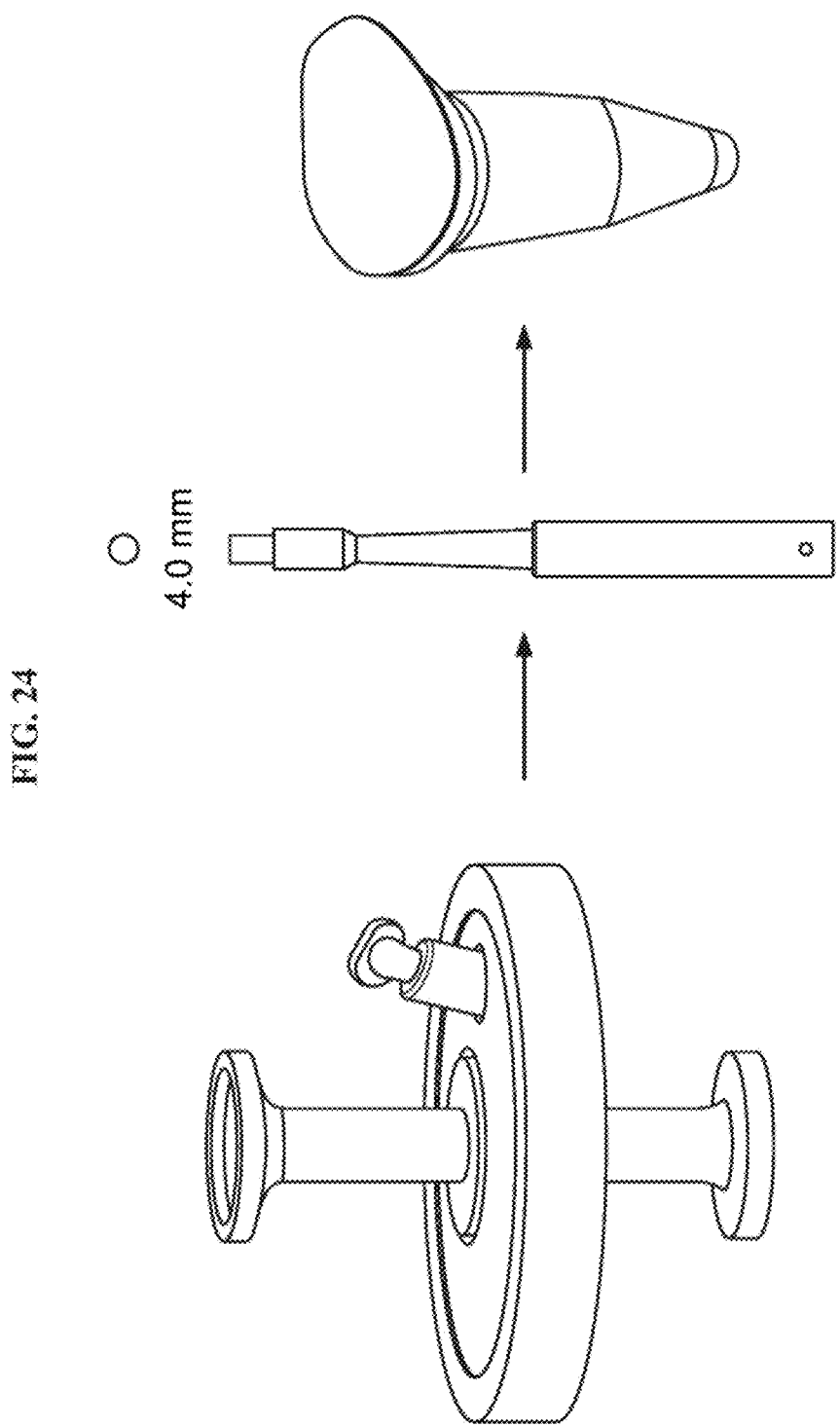
FIG. 24 shows excision of filter paper carried out according to an exemplary embodiment.

To evaluate what proteins precipitated over time, the filters were cut open and 4 mm discs were analyzed (See FIG. 24). The cut filter was immersed into 8M Urea and 10 mM TCEP-HCl and incubated at 50° C. for 30 minutes to dissolve, denature, and reduce the protein on the cut filter. The samples were then incubated with 10 mM indole-3-acetic acid (IAA) at RT for 30 minutes. The incubate samples were digested with 1 µg of rLysC for 1 hour under denaturing condition, followed by dilution with Tris-HCl. To this mixture, 1 µg of trypsin was added and the digestion was continued for 3 hours. The digestion mixture was then acidified with 20% formic acid (FA) followed by nanoLC-MS/MS analysis. The protein abundance was based on the average of mass spectrometry signal abundance of the top three peptide ions that assigned to a specific protein.

Figure 25:
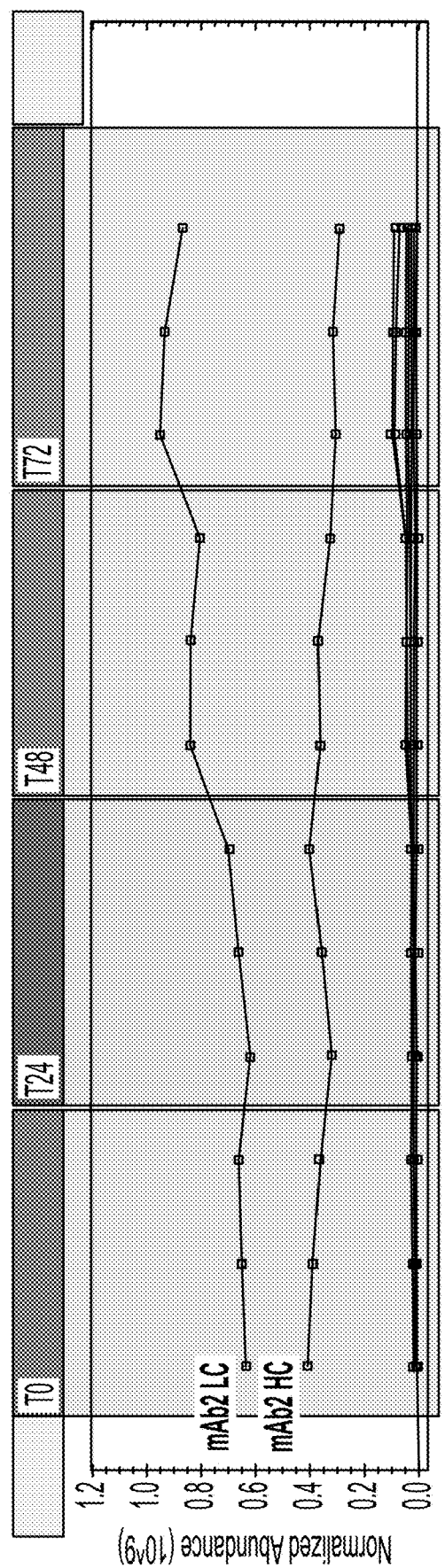
FIG. 25 shows a graph of normalized abundance of heavy chain and light chain of mAb2 in particles over 72 hours for a particle comprising mAb2 carried out according to an exemplary embodiment.

A total of 2366 quantifiable proteins were identified in the CCF of mAb2. From the identified proteins, 1880 proteins were included for further analysis (486 proteins were excluded because they showed less than two unique peptides per protein). The most abundant protein was mAb2. The abundance for mAb2 on the filter did not change over time (See FIG. 25 and Table 13).

TABLE 13

| Protein | Ratio T0/T0 | Ratio T24/T0 | Ratio T48/T0 | Ratio T72/T0 |
|---|---|---|---|---|
| mAb2 LC | 1.00 | 1.02 | 1.28 | 1.42 |
| mAb2 HC | 1.00 | 0.93 | 0.91 | 0.79 |

The average abundance of mAb2 LC was set to 1E6 and abundance of other proteins was calculated using HCP peptide mass spectrometer peak areas were normalized against the average abundance of mAb2 LC. The top fifty most abundant proteins (listed in Table 14) were closely examined since they are more likely to clog the filters.

TABLE 14

| # | Accession | Description | MW (Kda) | Calc. pI | Relative Amount to mAb2 LC (ppm) | | | | Ratio of | | |
|---|---|---|---|---|---|---|---|---|---|---|---|
| | | | | | T0 | T24 | T48 | T72 | T24/T0 | T48/T0 | T72/T0 |
| 1 | mAb2 LC | mAb2 LC | 23.5 | 8.29 | 849424.3 | 864288.0 | 1083370.2 | 1202917.5 | 1.0 | 1.3 | 1.4 |
| 2 | mAb2 HC | mAb2 HC | 48.9 | 6.37 | 506563.6 | 469802.7 | 460417.7 | 398929.1 | 0.9 | 0.9 | 0.8 |
| 3 | G3I1V3 | Fibronectin | 273.3 | 5.44 | 27041.7 | 30534.9 | 64162.5 | 125338.2 | 1.1 | 2.4 | 4.6 |
| 4 | Q9EPP7 | Cathepsin Z | 34.0 | 6.68 | 5524.6 | 5194.9 | 57941.1 | 104908.8 | 0.9 | 10.5 | 19.0 |
| 5 | G3HNJ3 | Clusterin | 51.7 | 5.51 | 34533.8 | 36067.1 | 50770.9 | 56806.0 | 1.0 | 1.5 | 1.6 |
| 6 | G3IBF4 | Serine protease HTRA1 | 28.7 | 6.54 | 12754.5 | 11588.1 | 37433.8 | 56748.6 | 0.9 | 2.9 | 4.4 |
| 7 | G3GVD0 | Actin, cytoplasmic 1 | 41.7 | 5.29 | 12927.6 | 16207.9 | 36190.2 | 47771.6 | 1.3 | 2.8 | 3.7 |
| 8 | Q9WV24 | Beta-2-microglobulin | 13.8 | 7.08 | 5227.7 | 5978.0 | 18710.8 | 44490.9 | 1.1 | 3.6 | 8.5 |
| 9 | G3IBH0 | Metalloproteinase inhibitor 1 | 22.4 | 8.74 | 1637.8 | 1482.0 | 14522.5 | 36234.4 | 0.9 | 8.9 | 22.1 |
| 10 | P17244 | Glyceraldehyde-3-phosphate dehydrogenase | 35.7 | 8.49 | 14332.1 | 17828.0 | 25183.3 | 29354.1 | 1.2 | 1.8 | 2.0 |
| 11 | G3H1W4 | Tubulointerstitial nephritis antigen-like | 52.5 | 6.73 | 16774.3 | 13111.5 | 19175.0 | 23409.9 | 0.8 | 1.1 | 1.4 |
| 12 | A0A061IKA1 | Lipoprotein lipase | 54.6 | 7.94 | 12714.5 | 12436.6 | 17956.6 | 20776.0 | 1.0 | 1.4 | 1.6 |
| 13 | G3HQY6 | Lipase | 45.6 | 7.43 | 11294.8 | 10967.2 | 16138.6 | 19445.8 | 1.0 | 1.4 | 1.7 |
| 14 | P62629 | Elongation factor 1-alpha 1 | 50.1 | 9.10 | 13770.0 | 14259.3 | 16568.8 | 19366.2 | 1.0 | 1.2 | 1.4 |
| 15 | G3I8R9 | 78 kDa glucose-regulated protein | 72.3 | 5.01 | 10128.8 | 25865.6 | 41706.4 | 17820.4 | 2.6 | 4.1 | 1.8 |
| 16 | G3GUR1 | Complement C1r-A subcomponent | 80.0 | 5.64 | 5376.2 | 5637.8 | 11704.9 | 17444.1 | 1.0 | 2.2 | 3.2 |
| 17 | G3HNF5 | Papilin (Fragment) | 127.2 | 7.27 | 463.9 | 490.3 | 4580.1 | 16039.8 | 1.1 | 9.9 | 34.6 |
| 18 | G3GXZ0 | Protein-glutamine gamma-glutamyltransferase 2 | 77.2 | 5.11 | 4526.0 | 6593.4 | 12121.1 | 14431.9 | 1.5 | 2.7 | 3.2 |
| 19 | G3I1Y9 | Sulfated glycoprotein 1 | 27.4 | 5.35 | 4288.9 | 3455.4 | 6153.1 | 11892.6 | 0.8 | 1.4 | 2.8 |
| 20 | A0A061I523 | Procollagen C-endopeptidase enhancer 1 | 50.4 | 7.94 | 5237.6 | 5455.5 | 9859.9 | 11552.8 | 1.0 | 1.9 | 2.2 |
| 21 | G3HLK3 | Granulins | 63.9 | 5.97 | 1541.7 | 1771.4 | 7858.8 | 10614.2 | 1.1 | 5.1 | 6.9 |
| 22 | G3HC84 | Heat shock protein HSP 90-beta | 47.8 | 5.32 | 3915.9 | 4483.9 | 9716.8 | 9920.4 | 1.1 | 2.5 | 2.5 |
| 23 | G3GUR0 | Calcium-dependent serine proteinase | 77.4 | 4.72 | 2204.4 | 2153.9 | 5351.9 | 9894.8 | 1.0 | 2.4 | 4.5 |
| 24 | G3HHV4 | Thrombospondin-1 | 60.0 | 4.25 | 4163.8 | 4863.3 | 7442.9 | 9109.5 | 1.2 | 1.8 | 2.2 |
| 25 | G3H1D5 | Carboxypeptidase | 51.2 | 5.30 | 4184.9 | 3967.5 | 6985.5 | 8678.0 | 0.9 | 1.7 | 2.1 |
| 26 | G3IAQ0 | Alpha-enolase | 46.7 | 5.85 | 4290.5 | 4413.4 | 6823.4 | 8376.7 | 1.0 | 1.6 | 2.0 |
| 27 | G3I4W7 | Cathepsin D | 44.1 | 6.59 | 3412.6 | 2873.9 | 4601.9 | 7320.9 | 0.8 | 1.3 | 2.1 |
| 28 | G3HDL6 | Elongation factor 1-beta | 24.7 | 4.50 | 2857.1 | 7716.5 | 9131.7 | 7289.8 | 2.7 | 3.2 | 2.6 |
| 29 | G3H8V4 | Phospholipid transfer protein | 54.3 | 6.24 | 4397.5 | 3564.0 | 5887.0 | 7227.7 | 0.8 | 1.3 | 1.6 |
| 30 | G3HEI6 | Lysyl oxidase-like 1 | 62.1 | 6.14 | 702.8 | 824.5 | 2371.9 | 6174.7 | 1.2 | 3.4 | 8.8 |
| 31 | G3H3E2 | Complement C1q tumor necrosis factor-related protein 1 | 35.6 | 7.77 | 95.2 | 1153.6 | 5031.2 | 6131.5 | 12.1 | 52.9 | 64.4 |

TABLE 14-continued

| # | Accession | Description | MW (Kda) | Calc. pI | Relative Amount to mAb2 LC (ppm) | | | | Ratio of | | |
|---|---|---|---|---|---|---|---|---|---|---|---|
| | | | | | T0 | T24 | T48 | T72 | T24/T0 | T48/T0 | T72/T0 |
| 32 | A0A061I5D1 | Heat shock cognate protein | 70.6 | 5.37 | 2472.1 | 4204.9 | 7601.5 | 5286.1 | 1.7 | 3.1 | 2.1 |
| 33 | A0A061IEA0 | Elongation factor 1-delta-like isoform 1 | 72.9 | 6.66 | 1918.6 | 4159.7 | 5562.9 | 5180.7 | 2.2 | 2.9 | 2.7 |
| 34 | G3HIQ1 | Peptidyl-prolyl cis-trans isomerase | 17.9 | 8.44 | 9127.8 | 7989.4 | 7293.1 | 4981.2 | 0.9 | 0.8 | 0.5 |
| 35 | A0A061IC58 | Elongation factor 1-gamma | 51.7 | 6.38 | 2770.1 | 4803.2 | 5660.0 | 4649.3 | 1.7 | 2.0 | 1.7 |
| 36 | G3GTT2 | C-C motif chemokine | 15.8 | 9.39 | 1933.9 | 1795.2 | 3154.8 | 4609.6 | 0.9 | 1.6 | 2.4 |
| 37 | G3HRK9 | Matrix metalloproteinase-19 | 58.9 | 7.81 | 2621.2 | 2496.7 | 3902.4 | 4481.2 | 1.0 | 1.5 | 1.7 |
| 38 | G3H3E4 | Galectin-3-binding protein | 63.8 | 5.05 | 4876.8 | 5402.7 | 3752.6 | 4400.0 | 1.1 | 0.8 | 0.9 |
| 39 | A0A098KXC0 | Pyruvate kinase | 81.4 | 8.59 | 2771.2 | 2823.6 | 3984.9 | 4374.1 | 1.0 | 1.4 | 1.6 |
| 40 | G3HTE5 | Lysosomal alpha-glucosidase | 105.8 | 5.65 | 2163.0 | 2207.5 | 3525.0 | 4352.6 | 1.0 | 1.6 | 2.0 |
| 41 | Q9JKY1 | Peroxiredoxin-1 | 22.2 | 8.21 | 3376.6 | 3373.7 | 4327.3 | 4331.9 | 1.0 | 1.3 | 1.3 |
| 42 | G3H8F4 | Dystroglycan | 96.8 | 8.70 | 1733.3 | 1889.3 | 2976.1 | 4324.7 | 1.1 | 1.7 | 2.5 |
| 43 | A0A061I2S4 | Putative out at first protein like protein (Fragment) | 23.5 | 5.42 | 1138.2 | 1224.6 | 2957.2 | 4316.1 | 1.1 | 2.6 | 3.8 |
| 44 | G3HBI1 | Peroxidasin-like | 165.3 | 6.49 | 1003.0 | 845.2 | 2640.4 | 4245.4 | 0.8 | 2.6 | 4.2 |
| 45 | G3H0L9 | Cathepsin B | 37.5 | 5.73 | 2070.2 | 1615.1 | 2211.7 | 3850.9 | 0.8 | 1.1 | 1.9 |
| 46 | G3IEB7 | Out at first protein-like | 17.7 | 8.38 | 927.5 | 1002.5 | 2925.0 | 3843.2 | 1.1 | 3.2 | 4.1 |
| 47 | G3HP49 | Tetranectin | 22.3 | 5.58 | 692.3 | 673.0 | 1734.3 | 3754.3 | 1.0 | 2.5 | 5.4 |
| 48 | G3IDM2 | Cofilin-1 | 18.5 | 8.22 | 2133.0 | 2177.6 | 2914.8 | 3634.8 | 1.0 | 1.4 | 1.7 |
| 49 | G3HWE4 | Nidogen-1 | 79.0 | 4.77 | 1316.4 | 1191.5 | 2274.9 | 3627.7 | 0.9 | 1.7 | 2.8 |
| 50 | G3H3E6 | Metalloproteinase inhibitor 2 | 21.5 | 7.47 | 205.8 | 229.8 | 1196.4 | 3609.7 | 1.1 | 5.8 | 17.5 |

Figure 26:
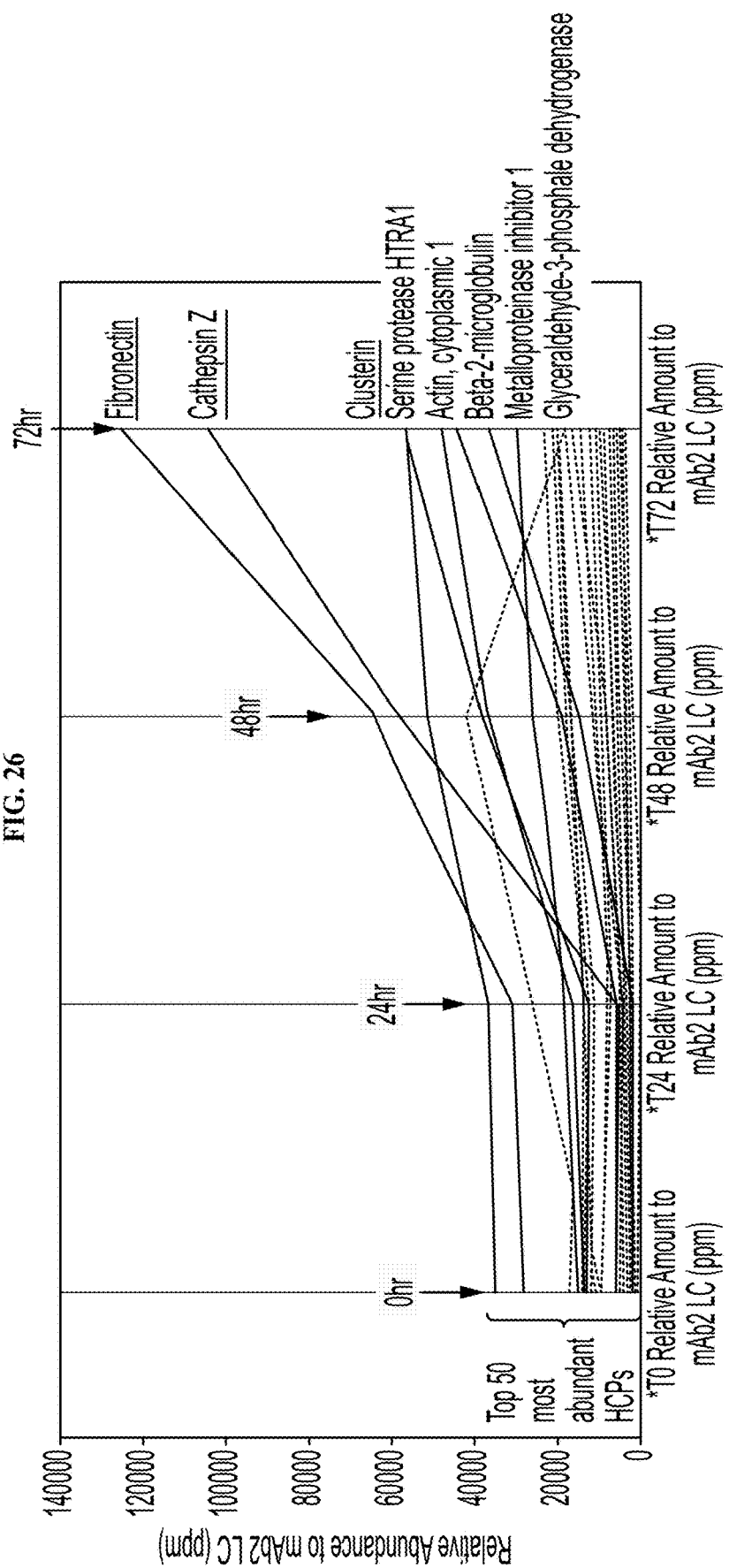
FIG. 26 shows a parallel plot of relative abundance of host cell proteins versus time for a particle comprising mAb2 carried out according to an exemplary embodiment.

A parallel plot of relative abundance of mAb2 versus time revealed that some of the high abundant HCPs increased over time (See FIG. 26).

Figure 27:
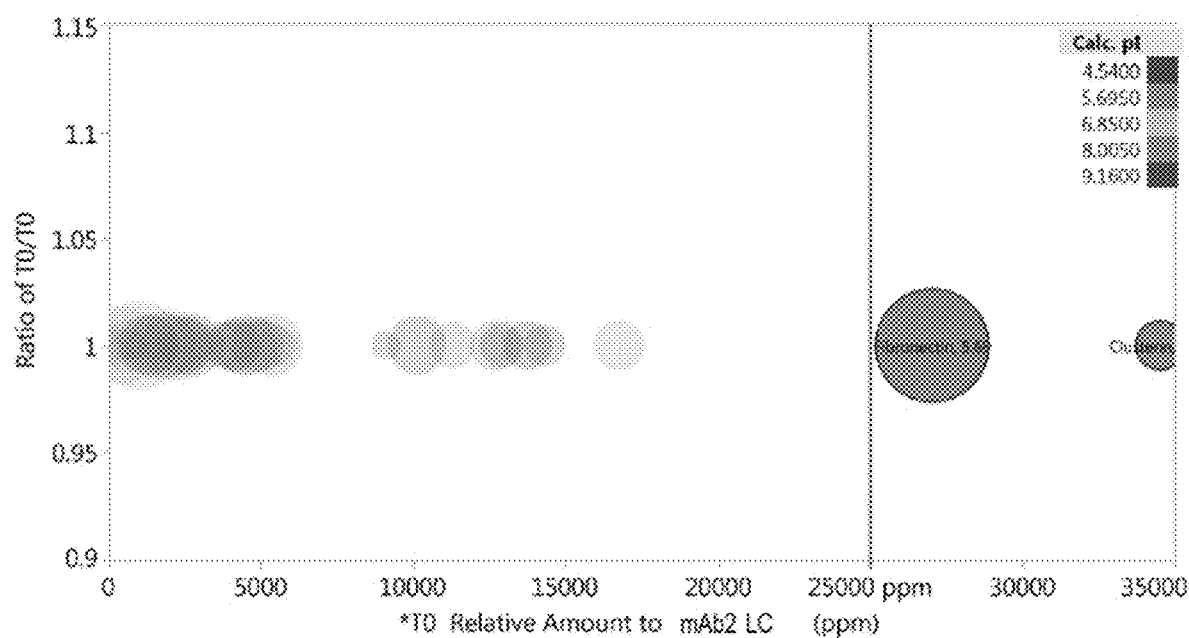
FIG. 27 shows a bubble plot of ratio of abundance of host-cell proteins in a particle at time T=0 hour to the host-cell proteins in the particle at time T=0 hour over relative amount of mAb2 in the particle at time T=0 hour carried out according to an exemplary embodiment.
Figure 28:
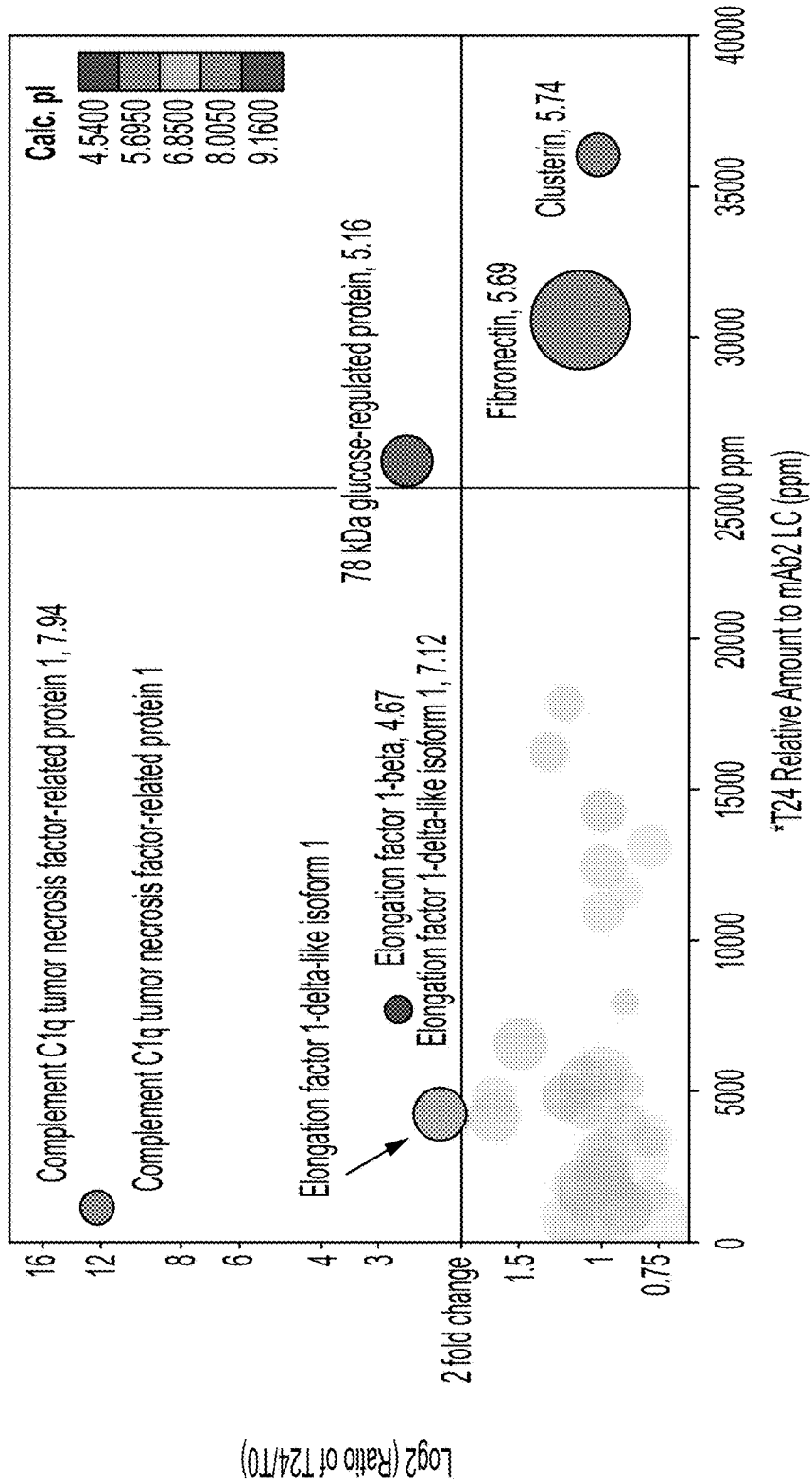
FIG. 28 shows a bubble plot of ratio of abundance of host-cell proteins in a particle at time T=24 hour to the host-cell proteins in the particle at time T=0 hours over relative amount of mAb2 in the particle at time T=24 hours carried out according to an exemplary embodiment.
Figure 29:
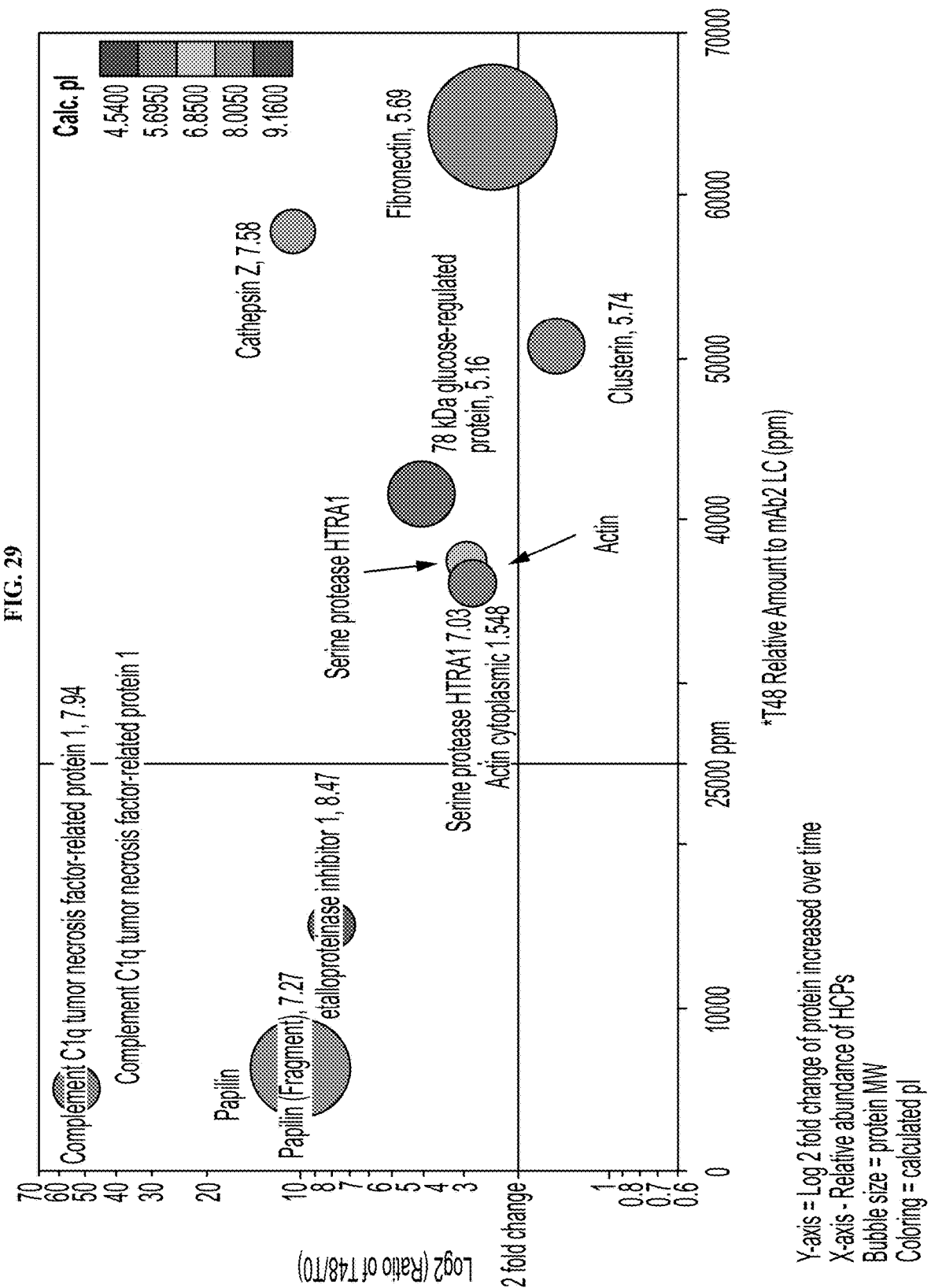
FIG. 29 shows a bubble plot of ratio of abundance of host-cell proteins in a particle at time T=48 hours to the host-cell proteins in the particle at time T=0 hour over relative amount of mAb2 in the particle at time T=48 hours carried out according to an exemplary embodiment.
Figure 30:
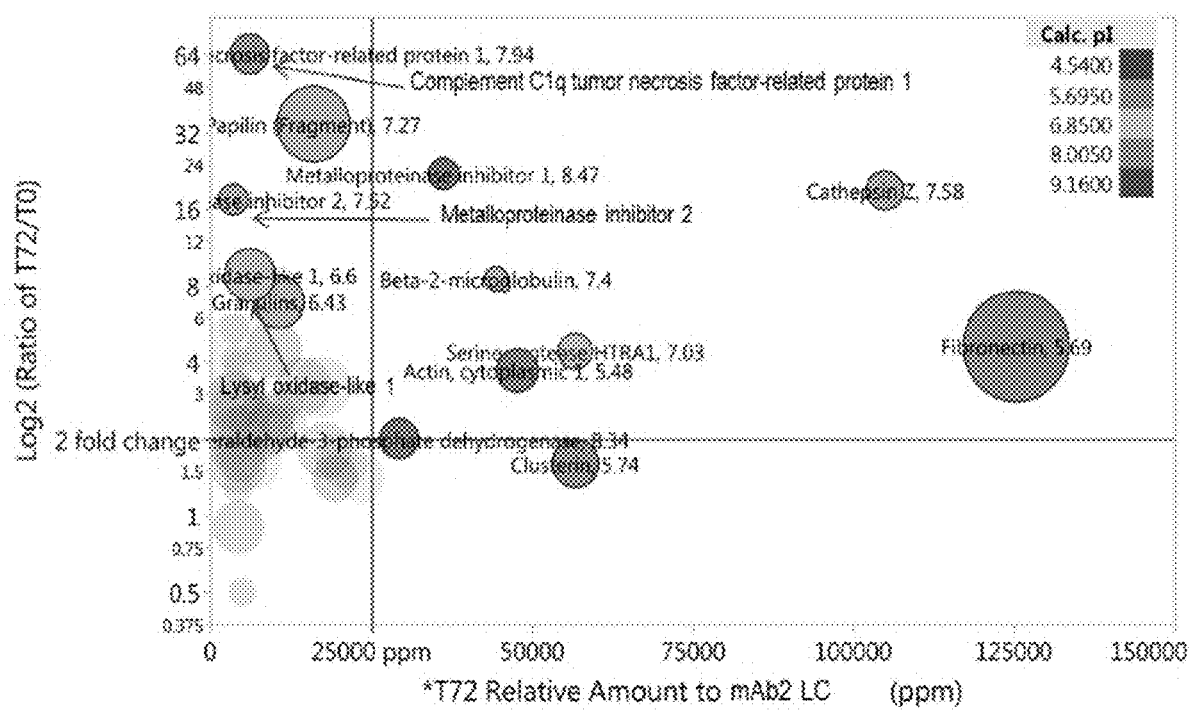
FIG. 30 shows a bubble plot of ratio of abundance of host-cell proteins in a particle at time T=72 hours to the host-cell proteins in the particle at time T=0 hour over relative amount of mAb2 in the particle at time T=72 hours carried out according to an exemplary embodiment.

In order to understand the amounts of HCPs precipitated in the incubated CCF filter at different time points, a bubble plot of the ratio of abundance of the HCP at a time T/abundance of the HCP at T0 versus relative amount of mAb2 LC at time T (ppm) is shown in FIG. 27 (T1=0 hours), FIG. 28 (T=24 hours). FIG. 29 (T=48 hour %), and FIG. 30 (T=72 hours). As seen in FIG. 28, a few of the HCPs (for example Complement C1q tumor necrosis, Elongation factor 1-beta, 78 kDa glucose-regulated protein and Elongation factor 1-delta-like isoform 1) increased over 2-fold which correlated to a moderated decrease in filter capacity. After 48 hours, a lot of the HCPs increased over 2-fold correlating to a similar significant decrease in filter capacity (See FIG. 29). At 72 hours, abundance at 72 hours for almost all of the top fifty HCPs increased over 2-fold compared to their abundance at 0 hour (See FIG. 30). For nine proteins form the top fifty HCPs increased over 5-fold compared to their abundance at 0 hour (Table 14).

Among the top fifty HCPs, Fibronectin showed a 4.6-fold increase at 72 hours and had the highest molecular weight and was possibly the most likely cause of decreased filter capacity.

Sub-visible or visible particles can lead to decreased filter capacity and finding the root cause for formation of sub-visible or visible particles or the root cause for decrease in filter capacity can be imperative for drug products or bioprocesses. Once the cause has been identified, steps can be taken to avoid it. The methods described herein can facilitate the identification of the root cause of formation of visible and sub-visible particles.

What is claimed is:

1. A method for characterizing a protein in at least one particle in a sample, comprising:
    (a) isolating at least one particle from a sample, wherein said at least one particle comprises at least one protein;
    (b) reducing said at least one isolated particle; and
    (c) subjecting said at least one isolated particle to mass spectrometry analysis to characterize said at least one protein.

2. The method of claim 1, wherein said at least one particle is a visible particle.

3. The method of claim 1, wherein said at least one particle is a subvisible particle.

4. The method of claim 1, wherein said at least one particle comprises a process-related impurity.

5. The method of claim 1, wherein said at least one particle comprises a recombinant protein.

6. The method of claim 5, wherein said recombinant protein is selected from a group consisting of an antibody, a bispecific antibody, a multispecific antibody, an antibody fragment, a monoclonal antibody, an Fc-fusion protein, or a therapeutic antibody.

7. The method of claim 5, wherein said recombinant protein is an antibody.

8. The method of claim 1, wherein said at least one particle comprises a product-related impurity.

9. The method of claim 1, wherein said at least one protein comprises a host cell protein.

10. The method of claim 1, wherein said sample is obtained from cell culture fluid, harvested cell culture fluid, drug substance, drug product, chromatographic eluate, or filtrate.

11. The method of claim 1, wherein said isolating comprises adding said at least one particle to a filter.

12. The method of claim 11, wherein said filter comprises a gold-coated polycarbonate membrane.

13. The method of claim 11, wherein a pore size of said filter is from 4 μm to 6 μm.

14. The method of claim 13, wherein said pore size is about 5 μm.

15. The method of claim 1, further comprising dissolving said at least one isolated particle prior to step (b).

16. The method of claim 15, wherein said dissolving comprises contacting said at least one isolated particle to urea.

17. The method of claim 16, wherein the concentration of said urea is about 8 M.

18. The method of claim 1, further comprising denaturing said at least one isolated particle prior to step (b).

19. The method of claim 18, wherein said denaturing comprises contacting said at least one isolated particle to urea.

20. The method of claim 1, wherein said reducing comprising contacting said at least one isolated particle to dithiothreitol (DTT) or tris(2-carboxyethyl)phosphine (TCEP).

21. The method of claim 1, further comprising digesting said at least one isolated particle prior to step (b).

22. The method of claim 21, wherein said digesting comprises contacting said at least one isolated particle to at least one hydrolyzing agent selected from a group consisting of trypsin, LysC, endoproteinase Arg-C, endoproteinase Asp-N, endoproteinase Glu-C, outer membrane protease T (OmpT), immunoglobulin-degrading enzyme of *Streptococcus pyogenes* (IdeS), chymotrypsin, pepsin, thermolysin, papain, pronase, protease from *Aspergillus Saitoi*, variants thereof, and a combination thereof.

23. The method of claim 21, wherein said digesting comprises contacting said at least one isolated particle to trypsin and LysC.

24. The method of claim 1, further comprising subjecting said at least one isolated particle to liquid chromatography separation prior to mass spectrometry analysis, wherein the mass spectrometer is coupled to the liquid chromatography system.

25. The method of claim 24, wherein said liquid chromatography system is a nano liquid chromatography system.

26. The method of claim 1, wherein said mass spectrometer is a tandem mass spectrometer.

* * * * *